United States Patent
Ezrin

(10) Patent No.: US 11,513,125 B2
(45) Date of Patent: Nov. 29, 2022

(54) MICROVESICLE HISTONE H2AX AS A BIOMARKER FOR GENOTOXIC STRESS

(71) Applicant: Pioma Inc., Miama, FL (US)

(72) Inventor: Alan M. Ezrin, Miami, FL (US)

(73) Assignee: PIOMA, INC., Miami, FL (US)

( * ) Notice: Subject to any disclaimer, the term of this patent is extended or adjusted under 35 U.S.C. 154(b) by 276 days.

(21) Appl. No.: 14/774,105

(22) PCT Filed: Mar. 14, 2014

(86) PCT No.: PCT/US2014/028079
§ 371 (c)(1),
(2) Date: Sep. 9, 2015

(87) PCT Pub. No.: WO2014/152873
PCT Pub. Date: Sep. 25, 2014

(65) Prior Publication Data
US 2016/0041175 A1 Feb. 11, 2016

Related U.S. Application Data

(60) Provisional application No. 61/785,552, filed on Mar. 14, 2013.

(51) Int. Cl.
| | |
|---|---|
| G01N 33/543 | (2006.01) |
| G01N 33/574 | (2006.01) |
| G01N 33/68 | (2006.01) |
| C12Q 1/6883 | (2018.01) |
| C12Q 1/6886 | (2018.01) |

(52) U.S. Cl.
CPC ..... *G01N 33/57496* (2013.01); *C12Q 1/6883* (2013.01); *C12Q 1/6886* (2013.01); *G01N 33/6875* (2013.01); *C12Q 2600/142* (2013.01); *C12Q 2600/158* (2013.01); *G01N 2333/4703* (2013.01); *G01N 2440/14* (2013.01); *G01N 2800/7004* (2013.01)

(58) Field of Classification Search
None
See application file for complete search history.

(56) References Cited

U.S. PATENT DOCUMENTS

| | | | |
|---|---|---|---|
| 6,812,023 B1 | 11/2004 | Lamparski et al. | |
| 6,899,863 B1 | 5/2005 | Dhellin et al. | |
| 2013/0203081 A1* | 8/2013 | Rak | G01N 33/5748 435/7.23 |
| 2014/0045915 A1* | 2/2014 | Skog | C12Q 1/6806 514/44 A |
| 2015/0140123 A1* | 5/2015 | Mueller | G01N 33/5014 424/649 |

FOREIGN PATENT DOCUMENTS

| | | |
|---|---|---|
| EP | 2202522 A1 | 6/2010 |
| WO | 2012/168184 A2 | 12/2012 |

OTHER PUBLICATIONS

Luminex xMAP technology (retrieved from https://www.ablinc.com/immunology-services/luminex/ on Jul. 8, 2017).*
Clingen et al., "Histone H2AX phosphorylation as a molecular pharmacological marker for DNA interstrand crosslink cancer chemotherapy", Biochemical Pharmacology, vol. 76, No. 1, Jul. 2008, pp. 19-27.
Dickey et al., "H2AX: Functional Roles and Potential Applications", Chromosoma, vol. 118, No. 6, Dec. 2009, pp. 683-692.
Extended European Search Report received for European Patent Application No. 14767965.8, dated Dec. 16, 2016, 8 Pages.
Mah et al., "YH2AX: a sensitive molecular marker of DNA damage and repair", Leukemia, vol. 24, 2010, pp. 679-686.
Palma et al., "MicroRNAs are Exported from Malignant Cells in Customized Particles", Nucleic Acids Research, vol. 40, No. 18, 2012, pp. 9125-9128.
International Preliminary Report on Patentability received for PCT Patent Application No. PCT/US2014/028079, dated Sep. 24, 2015, 7 pages.
International Search Report and Written Opinion received for PCT Patent Application No. PCT/US2014/28079, dated Jul. 11, 2014, 9 pages.
Pommier et al., "The Indenoisoquinolines Non-Camptothecin Topoisomerase I Inhibitors: Update and Perspectives", Mol Cancer Ther, vol. 8, No. 5, May 2009, pp. 1008-1014.
Zhang et al., "Temozolomide: Mechanisms of Action, Repair and Resistance", Current Molecular Pharmacol, vol. 5, No. 1, 2012, pp. 102-114.
Anderson et al., "The Human Plasma Proteome", Molecular & Cellular Proteomics, vol. 1, No. 11, Oct. 29, 2002, pp. 845-867.
Bard et al., "Proteomic Analysis of Exosomes Isolated from Human Malignant Pleural Effusions", Am J Respir Cell Mol Biol. vol. 31, 2004, pp. 114-121.
Botelho et al., "Top-Down and Bottom-Up Proteomics of SDS-Containing Solutions Following Mass-Based Separation", Journal of Proteome Research, vol. 9, No. 6, 2010, pp. 2863-2870.
Brown, Corrie, "Antigen Retrieval Methods for Immunohistochemistry", Toxicologic Pathology, vol. 26, No. 6, 1998, pp. 830-831.
Caby et al., "Exosomal-Like Vesicles are Present in Human Blood Plasma", International Immunology, vol. 17, No. 7, 2005, pp. 879-887.
Cheruvanky et al., "Rapid Isolation of Urinary Exosomal Biomarkers using a Nanomembrane Ultrafiltration Concentrator", Am. J. Physiol. Renal. Physiol., vol. 292, No. 5, May 2007, pp. F1657-F1661.
Choi et al., "Proteomic Analysis of Microvesicles Derived from Human Colorectal Cancer Cells", Journal of Proteome Research, vol. 6, No. 12, 2007, pp. 4646-4655.
Cocucci et al., "Enlargeosome Traffic: Exocytosis Triggered by Various Signals Is Followed by Endocytosis, Membrane Shedding or Both", Traffic, vol. 8, 2007, pp. 742-757.
Egger et al., "Protein (Western) Blotting", Molecular Biotechnology, vol. 1, 1994, pp. 289-305.
Gercel-Taylor et al., "Nanoparticle Analysis of Circulating Cell-Derived Vesicles in Ovarian Cancer Patients", Analytical Biochemistry, vol. 428, 2012, pp. 44-53.

(Continued)

*Primary Examiner* — Gary Counts
(74) *Attorney, Agent, or Firm* — Cooley LLP

(57) ABSTRACT

The invention described herein relates to methods of monitoring genotoxic stress in a test subject, specifically by detecting the expression level of microvesicle-associated H2AX from a biological sample.

16 Claims, 4 Drawing Sheets

Specification includes a Sequence Listing.

(56) References Cited

OTHER PUBLICATIONS

Hegmans et al., "Proteomic Analysis of Exosomes Secreted by Human Mesothelioma Cells", American Journal of Pathology, vol. 164, No. 5, May 2004, pp. 1807-1815.

Huang, Ruo-Pan, "Detection of Multiple Proteins in an Antibody-based Protein Microarray System", Journal of Immunological Methods, vol. 255, 2001, pp. 1-13.

Laemmli, U K., "Cleavage of Structural Proteins during the Assembly of the Head of Bacteriophage T4", Nature, vol. 227, Aug. 15, 1970, pp. 680-685.

Laterza et al., "Identification of Novel Brain Biomarkers", Clinical Chemistry, vol. 52, No. 9, 2006, pp. 1713-1721.

Liu et al., "A Model for Random Sampling and Estimation of Relative Protein Abundance in Shotgun Proteomics", Analytical Chemistry, vol. 76, 2004, pp. 4193-4201.

Mears et al., "Proteomic Analysis of Melanoma-Derived Exosomes by Two-Dimensional Polyacrylamide Gel Electrophoresis and Mass Spectrometry", Proteomics, vol. 4, 2004, pp. 4019-4031.

Nagrath et al., "Isolation of Rare Circulating Tumour Cells in Cancer Patients by Microchip Technology", Nature, vol. 450, No. 7173, Dec. 20, 2007, pp. 1235-1239.

Onorato et al., "Immunohistochemical and ELISA Assays for Biomarkers of Oxidative Stress in Aging and Disease", Annals New York Academy of Sciences, vol. 854, Nov. 1998, pp. 277-290.

Raposo et al., "B Lymphocytes Secrete Antigen-Presenting Vesicles", J. Exp. Med., vol. 183, Mar. 1996, pp. 1161-1172.

Simpson et al., "Proteomic Profiling of Exosomes: Current Perspectives", Proteomics, vol. 8, 2008, pp. 4083-4099.

Taylor et al., "MicroRNA Signatures of Tumor-Derived Exosomes as Diagnostic Biomarkers of Ovarian Cancer", Gynecologic Oncology, vol. 110, 2008, pp. 13-21.

Wubbolts et al., "Proteomic and Biochemical Analyses of Human B Cell-Derived Exosomes: Potential Implications fortheir Function and Multivesicular Body Formation", Journal of Biological Chemistry, vol. 278, No. 13, Mar. 28, 2003, pp. 10963-10972.

Duijvesz et al., "Proteomic Profiling of Exosomes Leads to the Identification of Novel Biomarkers for Prostate Cancer," PLOS ONE, Dec. 2013, vol. 8, Issue 12, pp. 1-10.

\* cited by examiner

SEQUENCE LISTING

```
<160> NUMBER OF SEQ ID NOS: 1

<210> SEQ ID NO 1
<211> LENGTH: 27
<212> TYPE: PRT
<213> ORGANISM: Artificial Sequence
<220> FEATURE:
<223> OTHER INFORMATION: Synthetic Construct

<400> SEQUENCE: 1

Leu Lys Leu Phe Glu Gly Leu Thr Leu Ala Gly Trp Ser Phe Arg Ser
1               5                   10                  15

Leu Ser Leu Gly Arg Gly Lys Gly Gln Ser Pro
            20                  25
```

MICROVESICLE HISTONE H2AX AS A BIOMARKER FOR GENOTOXIC STRESS

CROSS-REFERENCE TO RELATED APPLICATION(S)

This application is a U.S. National Stage of PCT/US2014/028079 filed Mar. 14, 2014, which claims the benefit of U.S. Provisional Application No. 61/785,552 filed Mar. 14, 2013, which are hereby incorporated herein by reference in their entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 674982000900SEQLIST.txt, date recorded: Aug. 23, 2017, size: 1 KB).

FIELD

The present disclosure relates to methods of monitoring genotoxic stress in a test subject, specifically by detecting the expression level of microvesicle-associated H2AX from a biological sample.

BACKGROUND

Agents that damage DNA or interfere with replication can be present in the environment, accidentally released, and/or intentionally administered. Exposure to these agents causes genotoxic stress in a wide variety of organisms. To assess the extent of damage/interference and whether such effects outweigh potential benefits arising from use of the agent, it is necessary to monitor, detect and/or measure genotoxic stress.

Agents that damage DNA or interfere with replication are commonly administered as a part of cancer treatment. Cancer is a leading cause of death worldwide. In 2004, it accounted for 7.4 million deaths (around 13% of all deaths). Deaths from cancer are expected to continue to rise, with a predicted 12 million deaths in 2030 (WHO, February 2009). Various treatments are available for cancer patients, such as chemotherapy, radiation, surgery, and drug therapy. Effective monitoring of cancer progression and treatment efficacy are critical to reducing the worldwide cancer burden, yet the development of robust and non-invasive methods and tools for monitoring disease progression and treatment efficacy remain major challenges in the field. Furthermore, a large proportion of patients with cancer, such as breast cancer and prostate cancer, are over-treated, resulting in wasted time and expense and unnecessary exposure of patients to unpleasant treatments and dangerous side effects (Hartmann et al., Lancet 2010, 11: 383-390). Effective, non-invasive monitoring of a patient's response to a treatment would greatly improve the efficiency of cancer management.

For many types of cancers, the current means of monitoring the efficacy of a given treatment of cancer in the patient involve histopathology of a tissue sample or imaging studies, which involve painful and invasive biopsies or risks associated with imaging such as exposure to radiation. These processes are often uncomfortable, expensive and inaccurate due to subjective interpretation by different technicians and clinicians. Thus, a need remains for sensitive, non-invasive, and rapid means for monitoring the efficacy of a given treatment for cancer patients.

Expression levels of specific proteins have been shown to have potential as an informative and reliable tool for making diagnoses, monitoring the efficacy of cancer treatment, and predicting prognoses. However, very few protein diagnostic markers have been developed to date (Anderson and Anderson, Mol Cell Proteomics 2002, 1.11: 845-867; Sanchez-Carbayo, Tumor Biol 2010, 31: 103-112).

An unmet need exists in the field of cancer biology for better methods of monitoring the efficacy of treatment in cancer patients. Ideally these methods would be less invasive and less painful and discomforting than are currently available monitoring techniques.

BRIEF SUMMARY OF PREFERRED EMBODIMENTS

The invention described herein meets the needs described above by providing methods of monitoring genotoxic stress in a test subject, specifically by detecting the expression level of microvesicle-associated H2AX in a biological sample. The H2AX to be detected may either be unphosphorylated or phosphorylated. In certain embodiments the phosphorylated H2AX is γH2AX.

In some embodiments, the genotoxic stress is due to environmental contamination or radiation exposure. In other embodiments, the genotoxic stress is due to cancer treatment, such as administration of an anti-cancer agent or exposure to radiation. Thus, methods described herein include methods of monitoring genotoxic stress due to cancer treatment in a test subject by detecting the expression level of microvesicle-associated H2AX in a test subject, and monitoring the cancer treatment in the subject based on the expression level of the microvesicle-associated H2AX. In some embodiments, detecting the expression level of microvesicle-associated H2AX in a biological sample from the test subject occurs at a plurality of time points following administration of the cancer treatment.

In certain embodiments of the above aspect, the cancer treatment includes administration of an anti-cancer agent such as a platinum analogue, a tetrazine, an anti-metabolite, a plant alkaloid or terpenoid, a cytotoxic antibiotic, a DNA alkylating agent (e.g., temozolomide), or a type I topoisomerase inhibitor (e.g., indenoisoquinoline).

In certain embodiments, monitoring the genotoxic stress involves comparing the expression level of H2AX in the biological sample from the test subject with the expression level of H2AX in a biological sample from a control subject that is not given the cancer treatment.

In certain embodiments, a higher level of expression of H2AX in the biological sample from the test subject compared to the level of expression of H2AX in the biological sample from the control subject may indicate that the cancer treatment is inhibiting replication of DNA in cancer cells in the test subject.

In some embodiments, monitoring the genotoxic stress involves evaluating the efficacy of the cancer treatment. In preferred embodiments, evaluating the efficacy of the cancer treatment in the test subject involves comparing the expression level of H2AX in the biological sample from the test subject with the expression level of H2AX in biological samples from a plurality of control subjects.

In certain embodiments, the plurality of control subjects have the same type of cancer as the test subject and are administered the same cancer treatment as the test subject.

In other preferred embodiments, the cancer treatment has a different level of treatment efficacy in each of the plurality of control subjects.

In some embodiments, a step is included for deriving a score from the comparison of the expression level of H2AX in the biological sample from the test subject with the expression level of H2AX in the biological samples from the plurality of control subjects, where the score indicates a level of similarity between the expression level of H2AX in the biological sample from the test subject and the expression level of H2AX in the biological samples from the plurality of control subjects. In preferred embodiments, determining the level of efficacy of the cancer treatment in the test subject is based on the above mentioned score. In additional preferred embodiments, the score used in determining the efficacy of the cancer treatment in the test subject is a correlation coefficient.

In preferred embodiments, the cancer in the above embodiments is a solid tumor. In other embodiments, the cancer is pancreatic, ovarian, adenocarcinoma, prostate, breast, brain, head, neck, cervical, or lymphoma cancers. The brain cancer can be glioblastoma multiforme (WHO grade III and IV) or lower grade malignancies including, for example, anaplastic astrocytoma, oligoastrocytoma, oligodendrogliomas; ependymoma, medulloblastoma, meningioma, pineal tumors, or pituitary tumors.

In certain embodiments, the biological sample in the above embodiments is plasma, serum, cerebrospinal fluid, urine, tears, milk, lymph fluid, synovial fluid, bronchoalveolar lavage, amniotic fluid, saliva, ocular fluid, ascites, and respiratory droplets.

In certain embodiments, detecting the expression level of H2AX involves detecting binding of H2AX to an H2AX-specific antibody. In preferred embodiments, the antibody is covalently bound to a bead. In yet additional preferred embodiments, detecting binding of H2AX to an H2AX-specific antibody involves detecting fluorescence. In other embodiments, detecting the expression level of microvesicle-associated H2AX involves the use of ELISA, flow cytometry, or liquid chromatography-mass spectrometry.

In certain embodiments, isolating microvesicles from the biological sample prior to detecting the expression level of H2AX involves contacting the biological sample with a cancer-derived microvesicle-specific reagent where the biological sample includes microvesicles and the reagent binds to the microvesicles, contacting the microvesicles with a tissue-specific reagent, and isolating the microvesicles derived from the tissue.

Certain aspects of the present disclosure relate to methods of monitoring genotoxic stress in a test subject by detecting the expression level of microvesicle-associated histone proteins in a biological sample from the test subject, and monitoring genotoxic stress in the subject based on the expression level of the microvesicle-associated histone protein.

DETAILED DESCRIPTION

Figure 1:
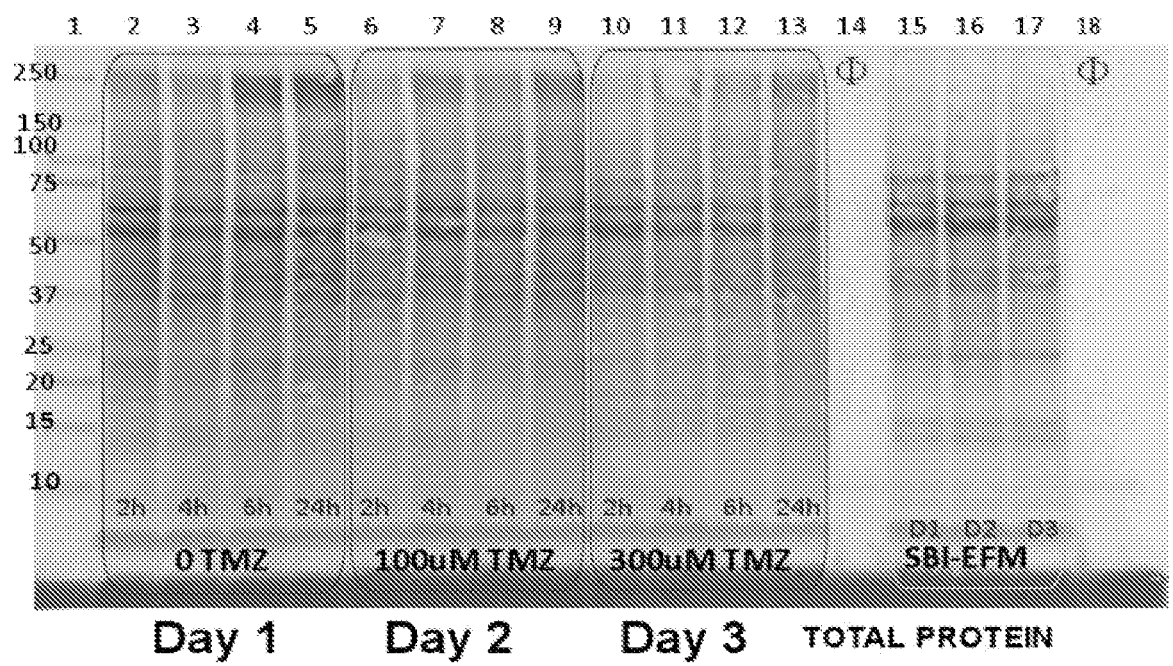
FIG. 1 illustrates a Western gel blot analysis of U87 brain tumor cell-shed microvesicle-derived total protein content from various microvesicle samples as a function of time or exposure to chemotherapeutic agent temozolomide (TMZ).

The present disclosure relates to methods of monitoring genotoxic stress in a test subject, specifically by detecting the expression level of microvesicle-associated H2AX, either unphosphorylated or in its phosphorylated form (e.g., γH2AX), in a biological sample.

Histones are proteins which package DNA into nucleosomes, the repeating units that make up chromatin. Histone H2A is one of the five types of histone proteins. There are several non-allelic variants of histone H2A. The variant histone H2AX has a C terminal tail that is used for DNA repair.

Without wishing to be bound by theory, it is believed that H2AX and γH2AX are markers for genotoxic stress due to the role that histones play in packaging DNA into nucleosomes. Furthermore, phosphorylation of histone H2AX to γH2AX (ser 139) is a robust early indicator of DNA damage such as double stranded breaks (DSBs).

Thus, the present disclosure includes the discovery of a non-invasive method for monitoring genotoxic stress in a test subject by detecting the expression level of H2AX associated with microvesicles.

Genotoxic stress in a test subject can be induced by a variety of circumstances, for example, accidental exposure of subjects to genotoxins (e.g., environmental contamination) or radiation, hostile exposure to genotoxins or radiation, and cancer treatment designed to slow or stop the growth of rapidly dividing cancer cells. It should be understood by one of skill in the art that the embodiments described herein with respect to methods for monitoring genotoxic stress due to cancer treatment are also embodiments of methods for monitoring genotoxic stress induced by other circumstances.

DEFINITIONS

In order to facilitate an understanding of the disclosure, selected terms used in the application will be discussed below.

"γH2AX" as used herein refers to a gamma-phosphorylated H2AX protein (i.e., phosphorylated on Serine 137). H2AX is a variant of the histone protein H2A.

When the term "H2AX" is used herein, it refers to all derivatives of H2AX, including both the unphosphorylated and phosphorylated forms of the protein. The phosphorylated residue of the derivative may be Serine 137 or another residue.

"Monitoring" as used herein refers to the act of observing. Monitoring a treatment may include observing a change in the expression level of a protein in an individual receiving that treatment over time.

"Microvesicle" as used herein refers to any small vesicle released from any cell type. Microvesicles include, for example, endosome-derived exosomes, plasma membrane-derived shedding vesicles, apoptotic bodies, prostasomes, P2 and P4 particles, and outer membrane vesicles (OMVs). Shedding vesicles may be referred to as ectosomes, microparticles, shedding bodies, exovesicles, or secretory vesicles. Protasomes may be referred to as aposomes or seminosomes. P2 and P4 particles may be referred to as prominosomes.

A "microvesicle-associated protein" as used herein refers to any protein that has been contained within or located on the surface of a microvesicle. "Microvesicle-associated protein" can refer to such a protein while the protein is still associated with a microvesicle or after the protein is no longer associated with a microvesicle. In preferred embodiments, the microvesicle-associated protein is γH2AX.

Monitoring Genotoxic Stress Due to Cancer Treatment
Monitoring Expression Levels of Microvesicle-Associated H2AX in Test and Control Subjects Described herein are methods of monitoring, detecting or measuring genotoxic stress due to cancer treatment, specifically by detecting the expression level of microvesicle-associated H2AX in a biological sample from a test subject.

The cancer treatment may be any treatment which is used to slow or stop the progression of the cancer. Such treatments may work via a wide variety of mechanisms ranging from alkylating DNA to interfering with other aspects of the DNA replication process. Exemplary methods include treatment with anti-cancer agents and/or exposure to radiation.

Anti-cancer agents include classical DNA alkylating agents such as temozolomide; nitrogen mustard; cyclophosphamide; mechlorethamine or mustine (HN2) (trade name Mustardgen); uramustine or uracil mustard; melphalan; chlorambucil; ifosfamide; nitrosoureas such as carmustine, lomustine and streptozocin; alkyl sulfonates such as busulfan; and Thiotepa. Certain alkylating agents are described as "non-classical". Examples of non-classical alkylating agents include procarbazine and altretamine.

Other anti-cancer agents are considered to be alkylating-like, since they do not have an alkylating group, but nevertheless damage DNA. Alkylating-like drugs include the platinum-based chemotherapeutic drugs (termed platinum analogues) such as cisplatin, carboplatin, nedaplatin, oxaliplatin, satraplatin, and triplatin tetranitrate, In some embodiments, the anti-cancer agent is a tetrazine, e.g., dacarbazine, mitozolomide, or temozolomide.

Other exemplary anti-cancer agents include anti-metabolites which mimic purines (e.g., azathioprine, mercaptopurine) or pyrimidines and become incorporated into the DNA.

Additional exemplary anti-cancer agents are the plant alkaloids and terpenoids, which block cell division by preventing microtubule function. The main examples of such anti-cancer agents are Vinca alkaloids and taxanes. The Vinca alkaloids include, without limitation, vincristine, vinblastine, vinorelbine, and vindesine. The taxanes include, without limitation, paclitaxel, originally known as Taxol and docetaxel. a semi-synthetic analogue of paclitaxel.

Anti-cancer agents also include topoisomerase inhibitors. Type I topoisomerase inhibitors include the camptothecins, irinotecan and topotecan. Type II inhibitors include amsacrine, etoposide, etoposide phosphate, and teniposide. These are semisynthetic derivatives of epipodophyllotoxins.

Anti-cancer agents also include cytotoxic antibiotics, for example, actinomycin, anthracyclines (e.g., doxorubicin, daunorubicin, valrubicin, idarubicin, epirubicin), bleomycin, plicamycin, and mitomycin.

In certain embodiments, the anti-cancer agents are DNA alkylating agents, such as temozolomide, or topoisomerase inhibitors, such as indenoisoquinoline, The indenoisoquinoline may include, without limitation, National Cancer Institute lead compounds NSC 706744, NSC 725776 (Indimitecan), NSC 724998 (Indotecan), as well as 6-Ethyl-5,6-dihydro-5,11-diketo-11H-indeno[1,2-c]isoquinoline, 5,6-Dihydro-5,11-diketo-6-propyl-11H-indeno[1,2-c]isoquinoline, 6-Cyclopropyl-5,6-dihydro-5,11-diketo-11H-indeno[1,2-c]isoquinoline, 5,6-Dihydro-5,11-diketo-6(methoxycarbonylmethyl)-11H-indeno[1,2-c]isoquinoline, 5,6-Dihydro-6-(4-hydroxy-1-butyl)-5,11-diketo11H-indeno[1,2-c]isoquinoline, 5,6-Dihydroxy-6-(5-hydroxy-1-pentyl)-5,11-diketo11H-indeno[1,2-c]isoquinoline, cis-4-Carboxy-3,4-dihydro-N-methyl-3-(3',4'methylenedioxyphenyl)-1(2H)isoquinolone, 5,6-Dihydro-5,11-diketo-6-methyl-8,9methylenedioxy-11H-indeno[1,2-c]isoquinoline, cis-N-(1-Butyl)-4-carboxy-3,4-dihydro-3-(3',4'methylenedioxyphenyl)-1(2H)-isoquinolone, 6-(1-Butyl)-5,6-dihydro-5,11-diketo-8,9methylenedioxy-11H-indeno[1,2-c]isoquinoline, cis-N-Ally-4-carboxy-3,4-dihydro-6,7-dimethoxy-3(3',4'-methylenedioxy phenyl)-1 (2H)isoquinolone, 6-Allyl-2,3-dimethoxy-5,6-dihydro-5,11-oxo-8,9(methylenedioxy)-11H-indeno[1,2c]isoquinoline, cis-N-(1-Butyl)-4-carboxy-3,4-dihydro-6,7dimethoxy-3-(3',4'methylenedioxyphenyl)-1(2H)isoquinolone, 6-(1-Butyl)-5,6-dihydro-5,11-diketo-2,3-dimethoxy8,9-methylenedioxy11H-indeno[1,2-c]isoquinoline, cis-N-Benzyl-4-carboxy-3,4-dihydro-6,7-dimethoxy3-(3',4'-methylenedioxyphenyl)-1(2H)isoquinolone, 6-Benzyl-5,6-dihydro-5,11-diketo 2,3-dimethoxy-8,9-methylenedioxy-11H-indeno[1,2-c]isoquinoline, cis-N-(p-Anisyl)-4-carboxy-3,4-dihydro-6,7dimethoxy-3-(3',4'-methylenedioxyphenyl)-1(2H)isoquinolone, 6-(p-Anisyl)-2,3-dimethoxy-5,6-dihydro-5,11diketo-8,9-methylenedioxy-11H-indeno[1,2-c]isoquinoline, cis-3-(3',4'-Dibenzyloxyphenyl)-4-carboxy-3,4dihydro-N-methyl-1-2H-isoquinolone, 8,9-Dibenzyloxy-5,6-dihydro-5,11-diketo-6-methyl11H-indeno[1,2-c]isoquinoline, cis-3-(3',4'-Dibenzyloxyphenyl)-4-carboxy-3,4dihydro-N-methyl-6,7-dimethoxy-1-(2H)-isoquinolone, 8,9-Dibenzyloxy-5,6-dihydro-5,11-diketo-6-methyl2,3-dimethoxy-11H-indeno[1,2-c]isoquinoline, cis-4-Carboxy-3,4-dihydro-N-methyl-6,7dimethoxy-3-(3',4',5'-trimethoxyphenyl)-1(2H) isoquinolone, 5,6-Dihydro-5,11-diketo-6methyl-2,3,8,9,10pentamethoxy-11H-indeno[1,c]isoquinoline, cis-4-Carboxy-3,4-dihydro-N-methyl-3(3',4', 5'trimethoxyphenyl)-1(2H)isoquinolone, 5,6-Dihydro-5,11-diketo-6-methyl-8,9,1Otrimethoxy-11H-indeno[1,2-c]isoquinoline, cis-4-Carboxy-N-ethyl-3-(3',4'-methylenedioxyphenyl)-6,7-dimethoxy3,4-dihydro-1(2H) isoquinolone, 6-Ethyl-5,6-dihydro-5,11-diketo-2,3-dimethoxy-8,9methylenedioxy-11H-indeno[1,2-c]isoquinoline, 5,6-Dihydro-5,11-diketo-6-(4-hydroxybut-1-yl)-2,3dimethoxy-8,9-methylenedioxy-(11H)indeno[1,2-c]isoquinoline, 5,6-Dihydro-6-(4-hydroxypent-1-yl)-5,11-diketo-2,3-dimethoxy-8,9-methylenedioxy-11Hindenoisoquinoline, cis-5,6,12,13-Tetrahydro-2,3-dimethoxy-6-methyl-5,11-dioxo-8,9(methylenedioxy)-(11H)indeno[1,2-c]isoquinoline, cis-6-Ethyl-5,6,12,13-tetrahydro-2,3-dimethoxy-5,11-dioxo-8,9-(methylenedioxy)-11H-indeno[1,2-c]isoquinoline, cis-6-Allyl-5,6,12,13-tetrahydro-2,3-dimethoxy-5,11-dioxo-8,9-(methylenedioxy)-(11H)indeno[1,2-c]isoquinoline, 5,6-Dihydro-5,11-diketo-2,3,8-trimethoxy-6-methyl9[(methylsulfonyl)oxy]-(11H)indeno[1,2-c]isoquinoline, 6-Ethyl-5,6,12a,13a-tetrahydro-11˜-hydroxy-2,3dimethoxy-8,9-(methylenedioxy)-5-oxo-11H-indeno[1,2-c]isoquinoline, 6-Ethyl-5,6,12a,13a-tetrahydro-11˜-hydroxy-2,3dimethoxy-8,9-(methylenedioxy)-11H-indeno[1,2-c]

isoquinoline, 6-(3-Carboxy-1-propyl)-5,6-dihydro-5,11-diketo11H-indeno[1,2-c]isoquinoline, or 6-Ethyl-2,3-dimethoxy-8,9-(methylenedioxy)-11Hindeno[1,2-c] isoquinolinium Chloride.

In certain embodiments, detecting the expression level of microvesicle-associated γH2AX in a biological sample from the test subject occurs at a plurality of time points following administration of the cancer treatment.

In certain embodiments, as disclosed herein, detecting the expression level of microvesicle-associated H2AX in a biological sample from the test subject following cancer treatment occurs at least after one day, at least after 3 days, at least after 4 days, at least after 5 days, at least after 6 days, at least after 7 days, at least after 8 days, at least after 10 days, at least after 12 days, at least after 14 days, at least after 16 days, at least after 18 days, at least after 20 days, at least after 21 days, at least after 25 days, at least after 30 days, at least after 2 months, at least after 4 months, at least after 6 months, at least after 8 months, at least or after 12 months.

In preferred embodiments, monitoring the cancer treatment involves comparing the expression level of H2AX in the biological sample from the test subject with the expression level of H2AX in a biological sample from a control subject that is not given the cancer treatment.

In certain embodiments, a higher level of expression of H2AX in the biological sample from the test subject compared to the level of expression of H2AX in the biological sample from the control subject indicates that the cancer treatment is inducing genotoxic stress in the test subject. Typically, an expression level is said to be increased or decreased relative to a second expression level if the difference between the two expression levels is statistically significant. The difference between two levels is considered to be statistically significant if it was unlikely to have occurred by chance. Statistical significance may be measured by any means known in the art, such as, for example, Fisherian statistical hypothesis testing or the Neyman-Pearson lemma.

In certain embodiments, monitoring the cancer treatment includes evaluating the efficacy of the cancer treatment in the test subject. Evaluating the efficacy may include methods of comparing the expression level of H2AX in the biological sample from the test subject with the expression level of H2AX in biological samples from a plurality of control subjects. Evaluating the efficacy may further include methods for assigning a score to the test subject based on expression levels of H2AX in test subjects compared to control subjects.

Typically, each of the plurality of control subjects has the same type of cancer as the test subject and is administered the same cancer treatment as the test subject.

In certain embodiments, the cancer treatment has a different level of treatment efficacy in each of the plurality of control subjects.

In certain embodiments, a step is included for deriving a score from the comparison of the expression level of H2AX in the biological sample from the test subject with the expression level of H2AX in the biological samples from the plurality of control subjects, where the score indicates a level of similarity between the expression level of H2AX in the biological sample from the test subject and the expression level of H2AX in the biological samples from the plurality of control subjects. In preferred embodiments, determining the level of efficacy of the cancer treatment in the test subject is based on the above mentioned score.

The score may be derived by any methods known to one of skill in the art. In certain embodiments, the score may simply be a measure of the difference in expression levels.

In preferred embodiments, the score is a correlation coefficient. A correlation coefficient describes the similarity between two expression patterns. Expression levels may be considered similar if the correlation coefficient is greater than or equal to 0.5. In preferred embodiments, for expression levels to be considered significantly similar, the correlation coefficient should be greater than 0.6, 0.7, 0.8, 0.9, or 0.95. In other embodiments, the score is generated by other statistical methods which produce a measure of mutual information to describe the similarity between two expression patterns. Expression levels may be considered similar if the normalized mutual information value is greater than or equal to 0.7. In preferred embodiments, for the expression levels to be considered significantly similar, the normalized mutual information value should be greater than 0.8, 0.9, or 0.95.

If the score indicates a significant level of similarity between the expression level of microvesicle-associated H2AX in the biological sample from the test subject and the expression level of microvesicle-associated H2AX in biological samples from the plurality of control subjects, then the test subject can be said to have or to be likely to have the same efficacy of cancer treatment as that of the plurality of control subjects. For example, if the score indicates a significant level of similarity between the expression level of H2AX in the biological sample from the test subject and the expression level of H2AX in biological samples from the plurality of control subjects who are not given the cancer treatment, then the cancer treatment can be said to be or likely to be efficacious.

Types of Cancer

The described methods may be applied to treatment of any type of cancer including, without limitation, adult acute lymphoblastic leukemia, childhood acute lymphoblastic leukemia, adult acute myeloid leukemia, childhood acute myeloid leukemia, adrenocortical carcinoma, childhood adrenocortical carcinoma, aids-related cancers, aids-related lymphoma, anal cancer, appendix cancer, basal cell carcinoma, extrahepatic bile duct cancer, bladder cancer, childhood bladder cancer, bone cancer, osteosarcoma and malignant fibrous histiocytoma, childhood brain stem glioma, adult brain tumor, childhood central nervous system atypical teratoid/rhabdoid tumor, childhood central nervous system embryonal tumors, childhood astrocytomas, childhood pineal parenchymal tumors of intermediate differentiation, childhood supratentorial primitive neuroectodermal tumors and pineoblastoma, childhood brain and spinal cord tumors, breast cancer, childhood breast cancer, male breast cancer, childhood bronchial tumors, burkitt lymphoma, childhood carcinoid tumor, primary central nervous system lymphoma, cervical cancer, childhood cervical cancer, childhood chordoma, chronic lymphocytic leukemia, chronic myelogenous leukemia, chronic myeloproliferative disorders, colon cancer, childhood colorectal cancer, childhood craniopharyngioma, childhood central nervous system embryonal tumors, endometrial cancer, childhood ependymoblastoma, childhood ependymoma, esophageal cancer, childhood esophageal cancer, Ewing sarcoma family of tumors, childhood extracranial germ cell tumor, extragonadal germ cell tumor, gallbladder cancer, gastric (stomach) cancer, childhood gastric (stomach) cancer, gastrointestinal carcinoid tumor, gastrointestinal stromal tumor (gist), childhood gastrointestinal stromal cell tumor, extragonadal germ cell tumor, ovarian germ cell tumor, gestational trophoblastic tumor, adult glioma, hairy cell leukemia, head and neck cancer, adult (primary) hepatocellular (liver) cancer, childhood (primary) hepatocellular (liver) cancer, adult Hodgkin lymphoma, childhood Hodgkin lymphoma, hypopharyngeal cancer, intraocular melanoma, islet cell tumors (endocrine pancreas), Kaposi sarcoma, kidney (renal cell) cancer, childhood kidney cancer, Langerhans cell histiocytosis, laryngeal cancer, childhood laryngeal cancer, chronic lymphocytic leukemia, chronic myelogenous leukemia, hairy cell leukemia, lip and oral cavity cancer, adult (primary) liver cancer, childhood (primary) liver cancer, non-small cell lung cancer, small cell lung cancer, adult non-Hodgkin lymphoma, childhood non-Hodgkin lymphoma, primary central nervous system lymphoma, Waldenström macroglobulinemia, malignant fibrous histiocytoma of bone and osteosarcoma, childhood medulloblastoma, childhood medulloepithelioma, melanoma, Merkel cell carcinoma, adult malignant mesothelioma, childhood mesothelioma, metastatic squamous neck cancer with occult primary, mouth cancer, childhood multiple endocrine neoplasia syndrome, multiple myeloma/plasma cell neoplasm, mycosis fungoides, myelodysplastic syndromes, myelodysplastic/myeloproliferative neoplasms, chronic myelogenous leukemia, multiple myeloma, chronic myeloproliferative disorders, nasal cavity and paranasal sinus cancer, nasopharyngeal cancer, childhood nasopharyngeal cancer, neuroblastoma, childhood oral cancer, oropharyngeal cancer, childhood ovarian cancer, ovarian epithelial cancer, ovarian germ cell tumor, ovarian low malignant potential tumor, pancreatic cancer, childhood pancreatic cancer, childhood papillomatosis, parathyroid cancer, penile cancer, pharyngeal cancer, pituitary tumor, plasma cell neoplasm/multiple myeloma, pleuropulmonary blastoma, prostate cancer, rectal cancer, respiratory tract carcinoma involving the nut gene on chromosome 15, retinoblastoma, childhood rhabdomyosarcoma, salivary gland cancer, childhood salivary gland cancer, adult soft tissue sarcoma, childhood soft tissue sarcoma, uterine sarcoma, Sézary syndrome, skin cancer (nonmelanoma), childhood skin cancer, skin cancer (melanoma), Merkel cell skin carcinoma, small intestine cancer, adult soft tissue sarcoma, childhood soft tissue sarcoma, squamous cell carcinoma, cutaneous t-cell lymphoma, testicular cancer, throat cancer, thymoma and thymic carcinoma, childhood thymoma and thymic carcinoma, thyroid cancer, childhood thyroid cancer, gestational trophoblastic tumor, transitional cell cancer of ureter and renal pelvis, urethral cancer, endometrial uterine cancer, uterine sarcoma, vaginal cancer, childhood vaginal cancer, vulvar cancer, or Wilms' tumor. The brain cancer can be glioblastoma multiforme (WHO grade III and IV) or lower grade malignancies including, for example, anaplastic astrocytoma, oligoastrocytoma, oligodendrogliomas; ependymoma, medulloblastoma, meningioma, pineal tumors, or pituitary tumors.

In some embodiments, treatment is for cancer that is a solid tumor. In other embodiments, the treatment is for a blood cancer such as leukemia, lymphoma, and myeloma. In certain embodiments, the cancer is selected from pancreatic, ovarian, adenocarcinoma, brain, prostate, breast, head, neck, or lymphoma cancers. In certain embodiments the cancer is a glioma, such as glioblastoma multiforme.

Detecting Expression Levels of Protein Biomarkers

Methods of the present disclosure include a step of detecting the expression level of microvesicle-associated H2AX, either when associated with the microvesicle or subsequent to dissociation from the microvesicle.

Protein level of H2AX is detected. In preferred embodiments, detecting the expression level of H2AX involves detecting binding of H2AX to an H2AX-specific antibody, e.g., ELISA. In additional preferred embodiments, the antibody is covalently bound to a bead. In yet additional preferred embodiments, detecting binding of H2AX to an H2AX-specific antibody involves detecting fluorescence. In other embodiments, the level of H2AX is measured directly, using for example, flow cytometry or a liquid chromatography-mass spectrometry.

In other embodiments, the method involves isolating cancer-derived microvesicles from the biological sample prior to detecting the expression level of H2AX. In preferred embodiments, isolating microvesicles from the biological sample prior to detecting the expression level of H2AX involves contacting the biological sample with a cancer-derived microvesicle-specific reagent where the biological sample includes microvesicles and the reagent binds to the microvesicles, contacting the microvesicles with a tissue-specific reagent, and isolating the microvesicles derived from the tissue.

The expression level of H2AX may include a relative or absolute amount of a protein in a sample, or it may simply refer to the presence or absence of a protein in a sample. The expression level of the microvesicle-associated H2AX may be detected by any methods known to one of skill in the art (see, for example: Coligan et al, Unit 9, *Current Protocols in Immunology*, Wiley Interscience, 1994), which include, without limitation: immunohistochemistry (*Microscopy, Immunohistochemistry and Antigen Retrieval Methods for Light and Electron Microscopy*, M. A. Hayat (Author), Kluwer Academic Publishers, 2002; Brown C.: "Antigen retrieval methods for immunohistochemistry," *Toxicol Pathol* 1998; 26(6): 830-1), ELISA (Onorato et al., "Immunohistochemical and ELISA assays for biomarkers of oxidative stress in aging and disease," *Ann NY Acad Sci* 1998 20; 854: 277-90), Western blotting (Laemmeli UK: "Cleavage of structural proteins during the assembly of the head of a bacteriophage T4," Nature 1970; 227: 680-685; Egger & Bienz, "Protein (western) blotting", *Mol Biotechnol* 1994; 1(3): 289-305), and antibody microarray hybridization (Huang, "Detection of multiple proteins in an antibody-based protein microarray system," *Immunol Methods* 2001 1; 255 (1-2): 1-13).

Typically, one of two approaches may be used in preparation for detecting the expression levels of the microvesicle-associated H2AX. In the first approach, the protein is dissociated from microvesicles. For example, the microvesicles are lysed, and the proteins in the microvesicles are extracted, precipitated, and reconstituted for analysis. In the second approach, the microvesicles are kept intact so that the protein remains associated, and the microvesicles are attached to a column, resin, or bead. The reconstituted protein or the microvesicles attached to a column, resin, or bead are used in the detection step. For example, the reconstituted protein or the microvesicles attached to a column, resin, or bead are contacted with an antibody specific to the H2AX biomarker.

In preferred embodiments, detecting the expression level includes detecting binding of H2AX to an antibody specific to this protein. Antibodies may be monoclonal or polyclonal, and they may be obtained from a commercial source or generated for use in the methods described herein. Methods for producing and evaluating antibodies are well known in the art, see, e.g., Coligan, (1997) *Current Protocols in Immunology*, John Wiley & Sons, Inc.; and Harlow and Lane (1989) *Antibodies: A Laboratory Manual*, Cold Spring Harbor Press, NY ("Harlow and Lane").

The antibody may be covalently bound to a bead or fixed on a solid surface, such as glass, plastic, or silicon chip. Typically, the biological sample is contacted with an antibody specific to H2AX. Any H2AX protein present in the sample will bind to the H2AX antibody. The mixture is washed, and the antibody-protein biomarker complexes can be detected. In preferred embodiments, H2AX is detected after the protein binds to an anti-H2AX antibody that is bound to a bead.

This detection can be achieved by contacting the washed antibody-protein biomarker complexes with a detection reagent. This detection reagent may be, for example, a secondary antibody which is labeled with a detectable label. Exemplary detectable labels include magnetic beads (e.g., DYNABEADS™), fluorescent dyes, radiolabels, enzymes (e.g., horseradish peroxide, alkaline phosphatase, and others commonly used in ELISA), and colorimetric labels such as colloidal gold, colored glass, or plastic beads. In preferred embodiments, H2AX is detected after the protein binds to an anti-H2AX antibody and includes detection of fluorescence.

Methods for measuring the amount of, or presence of, antibody-marker complexes include, for example, detection of fluorescence, luminescence, chemiluminescence, absorbance, reflectance, transmittance, birefringence, or refractive index (e.g., surface plasmon resonance, ellipsometry, a resonant mirror method, a grating coupler waveguide method, or interferometry). Optical methods include microscopy (both confocal and non-confocal), imaging methods, and non-imaging methods. Electrochemical methods include voltametry and amperometry methods. Radio frequency methods include multipolar resonance spectroscopy. Methods for performing these assays are readily known in the art. Useful assays include, for example, an enzyme immune assay (EIA) such as enzyme-linked immunosorbent assay (ELISA), a radioimmune assay (RIA), a Western blot assay, or a slot blot assay. These methods are also described in, e.g., *Methods in Cell Biology: Antibodies in Cell Biology*, volume 37 (Asai, ed. 1993); *Basic and Clinical Immunology* (Stites & Terr, eds., 7th ed. 1991); and Harlow & Lane, supra. In preferred embodiments, H2AX is detected after the protein binds to an anti-H2AX antibody and includes detection of fluorescence.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations, and the like. Usually the assays will be carried out at ambient temperature, although they can be conducted over a range of temperatures, such as 10° C. to 40° C.

Immunoassays can be used to determine the presence or absence of a marker in a sample as well as the quantity of a marker in a sample. The amount of an H2AX/anti-H2AX complex can be determined by comparing to a standard. A standard can be, e.g., a known compound or another protein known to be present in a sample. As noted above, the test amount of H2AX need not be measured in absolute units, as long as the unit of measurement can be compared to a control.

Biological Samples

The methods include detecting the expression level of microvesicle-associated H2AX in a biological sample from the test subject. The biological sample may be any sample from the body of the test subject that contains microvesicles. In preferred embodiments, the biological sample is a bodily fluid. As used herein, a "bodily fluid" refers to a sample of fluid isolated from anywhere in the body of the test subject, preferably a peripheral location, including but not limited to, for example, blood, plasma, serum, urine, sputum, spinal fluid, pleural fluid, nipple aspirates, lymph fluid, respiratory droplets, intestinal, and genitourinary tracts, tears, saliva, breast milk, fluid from the lymphatic system, semen, cerebrospinal fluid, intra-organ system fluid, ascitic fluid, tumor cyst fluid, synovial fluid, amniotic fluid, ocular fluid, ascites, bronchoalveolar lavage, and combinations thereof. In particularly preferred embodiments, the biological sample is blood. If the sample is blood, is it preferably centrifuged to remove cellular material and debris such that a plasma fraction is generated.

In especially preferred embodiments, the biological sample includes, but is not limited to, plasma, serum, cerebrospinal fluid, urine, tears, milk, lymph fluid, synovial fluid, bronchoalveolar lavage, amniotic fluid, saliva, ocular fluid, ascites, and respiratory droplets.

The H2AX detected in the methods are associated with microvesicles present in the biological sample. The microvesicles may be derived from endosomes (exosomes) or from the plasma membrane (shedding vesicles). The microvesicles may also be, for example, apoptotic bodies, prostasomes, P2 and P4 particles, or outer membrane vesicles (OMVs). The H2AX associated with the microvesicles may be membrane proteins or cytosolic proteins.

Isolation of Microvesicles

The methods may include a step of isolating microvesicles from the biological sample prior to detecting the expression level of H2AX. Various different populations of microvesicles may be isolated. For example, when the methods relate to detection of the expression level of H2AX expressed by all tissues, the entire population of microvesicles is isolated. When the methods relate to detection of the expression level of expressed by multiple tissues, a specific sub-population of microvesicles derived from these tissues is isolated. When the methods relate to detection of the expression level of protein biomarkers expressed by a single tissue, microvesicles derived from that specific tissue are isolated. In preferred embodiments, microvesicles from various tissues are isolated by contacting microvesicles with a tissue-specific reagent.

The entire population of microvesicles may be isolated according to any methods known to one of skill in the art (see, for example, Cocucci et al., *Traffic* 8, 2007: 742-757; Simpson et al., *Proteomics* 8, 2008: 4083-4099). In certain embodiments, isolating microvesicles involves centrifugation. For example, serial centrifugation may be used to remove cells and debris, and microvesicles may be pelleted using sedimentation at 60-100,000×g for 1 hour or longer. Additional methods of differential centrifugation are described in Raposo et al., *J Exp Med* 183, 1996: 1161-72. In other embodiments, techniques such as filtration, sucrose density gradients, organelle electrophoresis, anion exchange and/or gel permeation chromatography, magnetic activated cell sorting (MACS), nanomembrane ultrafiltration concentration, and microchips with microfluidic technology may be used to isolate microvesicles. For example, large cell debris may be removed by filtration with a 0.22 µm or a 0.1 µm filter. Microvesicles may be isolated by passing the biological sample through a filter having an average pore diameter of between 0.01 µm and about 0.15 µm. Linear sucrose gradients (2.0-0.25 M sucrose), or a combination of ultrafiltration (500 K membrane) and ultracentrifugation into a 30% sucrose/deuterium oxide (98%) cushion (density, 1.210 g/cm$^3$) may also be used. Various methods for the isolation of microvesicles can be found, for example, in U.S. Pat. Nos. 6,899,863, 6,812,023, Taylor and Gercel-Taylor, *Gynecol Oncol* 110, 2008: 13-21, Cheruvanky et al., *Am J Physiol Renal Physiol* 292, 2007: F1657-61, and Nagrath et al., *Nature* 450, 2007: 1235-9.

Isolation of Microvesicles Via Affinity Capture

In preferred embodiments, isolation of microvesicles is accomplished using affinity capture methods. Preferably, these affinity methods are immunoaffinity methods, but in certain embodiments, such methods employ other reagents which bind specifically to H2AX. Such methods can be a step in other methods prior to detection of H2AX described above.

As a first step, the entire population of microvesicles may be isolated by contacting biological samples containing microvesicles with a reagent specific to a protein commonly found on the surface of all microvesicles regardless of origin (i.e., microvesicle-specific reagents). In certain embodiments, the reagents are specific to the following proteins: membrane adhesion proteins (integrins), membrane transport/trafficking proteins (annexins and Rab proteins, such as Rab guanosine triphosphatase), cytoskeletal components (actin, tubulin, ERM proteins, lysosomal markers, and tetraspanin proteins, such as CD9, CD63, CD81, and CD82), antigen presenting proteins (HLA class I and II), death receptors, cytokines and cognate receptors (TNF, TNFR1, and TGF-β), iron transport proteins, enzymes (enolase), cytosolic proteins (Hsc73 and Hsc90), subunits of trimeric G proteins, Tsg101, milk-fat globule (MFG)-E8, lactadherin, MHC class I molecules, heat shock proteins (Hsp70 and Hsp90), drug transporter proteins, or signal transduction proteins. In certain embodiments, reagents are specific to microvesicles from specific cell types such as class II MHC and co-stimulatory molecules (CD86) from antigen-presenting cells, von Willebrand factor or CD41a (GPIIb) from platelets, TCR from T-cells, or perforin or granzyme from cytotoxic T cells (Caby et al., Inter Immunol 17(7); 879-887; 2005). Reagents specific for lipids on the surface of microvesicles may also be used. For example, in preferred embodiments, the immunoaffinity capture includes use of an anti-phosphatidylserine antibody which binds to microvesicles having phosphatidylserine molecules with the polar side of the molecule exposed on its outer surface. The antibody is preferably monoclonal, but can also be polyclonal. In other embodiments, the first step isolates a specific sub-population of microvesicles, for example, those derived from endosomes or those derived from plasma membrane using antibodies specific to these sub-populations.

Alternatively, as a first step, microvesicles may first be contacted with a reagent which binds specifically to microvesicles which are derived from a cancerous cell (i.e., cancer-derived microvesicle-specific reagent). Such a reagent may be one that binds only to microvesicles derived from cancerous cells or one that binds to any composition, such as a microvesicle, which displays certain cancer-specific proteins on its surface. If the reagent is the latter, the methods described herein will also include a step for isolating microvesicles or distinguishing them from other compositions found in the samples. Exemplary cancer-derived microvesicle-specific reagents include antibodies specific to tumor cell surface proteins or tumor antigen proteins. In certain embodiments, these proteins include tumor surface antigens, tumor invasion-related proteins, angiogenesis proteins, immune-suppressing cytokines, integrin proteins, and proteases. In certain embodiments, these proteins include cancer-specific cell-surface proteins such as those listed below in Table 1. Several studies have identified proteins specific to microvesicles derived from various tumor types (see, for example, Bard, M P et al., Am J Respir Cell Mol Biol. 2004 31(1):114-21; Hegmans, J P et al., Am J Pathol. 2004; 164(5):1807-15; Mears, R et al., Proteomics. 2004; 4(12):4019-31; and Choi, D S et al., J Proteome Res. 2007; 6(12):4646-55). These antibodies are preferably monoclonal, but can also be polyclonal. In preferred embodiments, the cancer-derived microvesicle-specific reagent is a reagent specific for phosphatidylserine, EGFRvIII, IDH1, PDGFRalpha, VEGFR, or $\alpha_V/\beta_{III}$ integrin.

TABLE 1

| Cancer-Specific Markers Cancer-Specific Markers | | |
|---|---|---|
| APC | HHAT | NRP2 |
| C18orf8 | HHIP | OTX2 |
| C6orf138 | IFT52 | PDGFC |
| CD44 | IHH | PGF |
| CDH1 | ITGA7 | PNN |
| CDH11 | ITGB3 | PTCH1 |
| CDH6 | KDR | PTCH2 |
| CDKN2A | KITLG | PTCHD1 |
| CDON | LAMR1 | PTCHD2 |
| CEP76 | MCAM | PTCHD3 |
| CTNNA1 | MGAT5 | RPSA |
| CTNNB1 | MMP10 | SHH |
| DHH | MMP11 | SIAH1 |
| FAT | MMP13 | SMO |
| FGF9 | MMP2 | SUFU |
| FIGF | MMP3 | SYK |
| FKBP8 | MMP7 | TGFB1 |
| FLT1 | MMP9 | TIMP2 |
| FLT4 | MTSS1 | TIMP3 |
| FN1 | NF1 | TIMP4 |
| FXYD5 | NF2 | VEGF |
| GLI1 | NPC1 | VEGFA |
| GLI2 | NPC1L1 | VEGFB |
| GLI3 | NRP1 | VEGFC |
| GSK3B | | |

In other embodiments, the cancer-derived microvesicle-specific reagent only binds to cancer-derived microvesicles derived from certain tissue types. In this case, the cancer-derived microvesicle-specific reagent is also a tissue-specific reagent.

Before, subsequent to, or at the same time as capture with a first microvesicle-specific or cancer-derived microvesicle-specific reagent, the microvesicles, either in isolated form or found in the biological sample, can be contacted with a tissue-specific reagent to isolate microvesicles derived from a specific tissue. Exemplary tissues of interest include brain, adrenal gland, endocrine gland, pituitary, hypothalamus, parathyroid, uterus, heart, blood vessel, stomach, trachea, pharynx, gums, hair, scalp, subcutaneous tissue, Fallopian tube, reproductive tract, urethra, skin, bone, stem cell, umbilical cord, placenta, lymphocyte, monocyte, macrophage, formed blood cell, smooth muscle, skeletal muscle, connective tissue, spinal cord, kidney, bladder, anus, bone, breast, prostate, lung, cervix, colon, rectum, uterus, esophagus, skin, liver, pharynx, mouth, neck, ovary, pancreas, lung, eye, intestine, mouth, thyroid, GI tract, and endometrium.

In certain embodiments, there is a third step of contacting the microvesicles with an organelle-specific reagent and isolating the microvesicles derived from organelles of cells in a specific tissue. Particular organelles of interest include plasma membrane, peroxisome, smooth ER, rough ER, lysosome, mitochondria, and nucleus.

In some embodiments, each step is performed using multiple microvesicle-specific, cancer-derived microvesicle-specific, or tissue-specific reagents.

In preferred embodiments, an anti-tenascin-C specific antibody is used to isolate microvesicles from brain tissue. In other preferred embodiments, microvesicles derived from certain tissues are isolated using antibodies to tissue markers known to those of skill in the art. For example, markers for brain tissue include VLP-1, synaptosomal-associated protein, GAD67, myelin-associated oligodendrocyte basic protein, synaptotagmin I, tubulin β 4, zygin, glycine receptor β, protein 1 kinase C and casein kinase subtrate in neurons 1, internexin neuronal intermediate filament protein α, neuroserpin, synaptobrevin 2, or neurogranin (Laterza et al.; *Clin Chem* 52:9; 1713-21; 2006).

In related embodiments, subsequent to capture with a first microvesicle-specific/cancer-derived microvesicle-specific reagent, the entire population of microvesicles is contacted with an reagent which binds to microvesicles derived from multiple tissue types rather than one that binds microvesicles derived from a specific tissue.

In preferred methods for isolating microvesicles derived from specific tissue(s), the method includes contacting a biological sample with an reagent specific for microvesicles, preferably a reagent specific for phosphatidylserine, wherein the biological sample includes microvesicles and the reagent binds to microvesicles; contacting the microvesicles with a tissue-specific reagent and then isolating the microvesicles derived from the tissue(s).

In particularly preferred embodiments, methods for isolating microvesicles derived from brain cancer tissue from blood include the steps of providing blood; providing plasma by centrifuging the blood; contacting plasma with an anti-phosphatidylserine antibody in a physiological buffer, wherein the anti-phosphatidylserine antibody binds to microvesicles; isolating microvesicles bound by the anti-phosphatidylserine antibody; contacting the microvesicles with an anti-tenascin antibody; and isolating the microvesicles derived from brain cancer tissue. Preferably, the plasma is contacted with an anti-phosphatidylserine antibody for about 60 minutes and the microvesicles are isolated by changing the ionic strength of the physiological buffer.

Affinity Steps

Contacting a biological sample with an microvesicle-specific reagent or cancer-derived microvesicle-specific reagent and contacting the microvesicles with a tissue-specific reagent may occur in a single step. Under such circumstances, the reagents may be coupled to the same solid support. Alternatively, the steps are performed sequentially. The biological sample is first contacted with a microvesicle-specific reagent/cancer-derived microvesicle-specific reagent and then contacted with a tissue-specific reagent, sometimes with an intervening step of isolating the microvesicles bound by a microvesicle-specific/cancer-derived microvesicle-specific reagent. The steps may also be reversed, such that biological sample is first contacted with a tissue-specific reagent and then a microvesicle-specific/cancer-derived microvesicle-specific reagent, sometimes with an intervening step of isolating a fraction bound by the tissue-specific reagent.

Contacting the biological sample and the reagents occurs for a suitable incubation time which optimizes the efficiency of the microvesicle/tissue marker:reagent interaction. It is well within the competence of one of ordinary skill in the art to determine the particular conditions based on the disclosure herein. Typically, the biological sample and reagents are incubated together in a suitable buffer at physiological pH at a suitable temperature (e.g., about 4-37° C.), for a suitable time period (e.g., about 60 minutes to overnight) to allow the binding to occur.

Once bound by reagent, microvesicles are isolated using standard methods known to those of skill in the art. For example, if the microvesicles are bound to an immunoaffinity resin, the resin is washed with physiological buffers, such as Tris-Acetate pH 7.6 to remove other unbound components of the biological sample and then eluted by changing the ionic strength of the buffer for the resin, for example, by gradually increasing the concentration of a salt, such as NaCl, $CaCl_2$, KCl, $MgCl_2$, or similar salts that cause the reagent to release the bound microvesicles. Sepharose 2B columns may also be used for size exclusion methodologies of isolating microvesicles (Taylor et al., 2012).

Solid Support and Column Configuration

The reagents are typically coupled to solid supports. A solid support, for purposes of the present disclosure, can be any material that is an insoluble matrix and can have a rigid or semi-rigid surface to an reagent can be linked or attached. Exemplary solid supports include, but are not limited to, substrates such as nitrocellulose, polyvinylchloride; polypropylene, polystyrene, latex, polycarbonate, nylon, dextran, chitin, sand, silica, pumice, agarose, cellulose, glass, metal, polyacrylamide, silicon, rubber, polysaccharides, polyvinyl fluoride, diazotized paper, activated beads, magnetically responsive beads, and any materials commonly used for solid phase synthesis, affinity separations, purifications, hybridization reactions, immunoassays and other such applications. The support can be particulate or can be in the form of a continuous surface and includes membranes, mesh, plates, pellets, slides, disks, capillaries, hollow fibers, needles, pins, chips, solid fibers, gels (e.g. silica gels) and beads, (e.g., pore-glass beads, silica gels, polystyrene beads optionally cross-linked with divinylbenzene, grafted co-poly beads, polyacrylamide beads, latex beads, dimethylacrylamide beads optionally crosslinked with N-N'-bis-acryloylethylenediamine, iron oxide magnetic beads, and glass particles coated with a hydrophobic polymer.

Typically, the solid support is a bead or resin in a column configuration. In preferred immunoaffinity capture methods for isolating microvesicles of interest, the method includes providing a column, applying a biological sample suspected of containing one or more of the microvesicles of interest to bind to resins in the column, washing the column, eluting the resins and analyzing the eluant for the presence of the microvesicles of interest. More specifically, such methods can include loading the column with a predetermined amount of a biological sample suspected of containing the microvesicles of interest in either blood plasma or a physiological buffer; binding the microvesicles to the reagent on the column; loading the column with a wash solution, suspending the resin in the wash solution; removing the wash solution from the column; eluting the microvesicles in eluant; and analyzing the eluant for the presence of the microvesicles.

In certain embodiments, it is preferred that that the column configuration used in such methods allows for suspension of the resin beads, such as a mobile bead column or other resin during washing. It has been discovered that such a column configuration results in significantly lower levels of background and hence more sensitive levels of quantitation and overall yield of the desired target.

In certain embodiments, the column used in such methods includes a lower end including an outflow opening; a lower porous support; a layer of resin on the lower porous support, the resin having specific affinity for all microvesicles or tissue-specific microvesicles; an upper porous support; and an upper end including an inflow opening; wherein the resin between the lower porous support and the upper porous support is structured and arranged to permit removal of the upper porous support from the column without substantial removal of resin.

In other embodiments, the resin is fixed between two semi-porous frits such that the resin beads may be suspended and such that the upper frit may be removed during washing of the resin to remove background compounds.

The volume of the resin in the column can vary but is typically less than the total packed volume of the column between the lower porous support and the upper porous support. Preferably, the volume of the resin in the column is no greater than 50%, more preferably no greater than 40%, even more preferably no greater than 30%, still more preferably no greater than 25%, and still more preferably no greater than 20% of the total packed volume of the column between the lower porous support and the upper porous support.

Analysis of H2AX Expression Levels

Described herein are methods of monitoring genotoxic stress due to cancer treatment in a test subject, specifically by detecting the expression level of microvesicle-associated H2AX.

In certain embodiments, methods include comparing the expression level of H2AX in the biological sample from the test subject with the expression level of H2AX in a biological sample from a control subject that is not given the cancer treatment. The expression levels from biological samples from the plurality of control subjects may be simultaneously obtained with the test subject expression levels or may constitute a set of numerical values stored on a computer or on computer readable medium. In preferred embodiments, the control subjects are of the same sex and of a similar age as the test subject. Control subjects may also be of a similar racial background as the test subject. Preferably, biological samples taken from the test subject and from the plurality of control subjects are of the same type, e.g., blood samples.

Comparison of the expression levels of the one or more microvesicle-associated H2AX in biological samples from the test subject and from a plurality of control subjects may be performed manually or automatically by a computer program. The expression level of H2AX in the biological sample from the test subject may be compared individually to the expression level of the microvesicle-associated H2AX from biological samples in each control subject, or the expression level of microvesicle-associated H2AX in the biological sample from the test subject may be compared to an average of the expression levels from biological samples from the plurality of control subjects. In certain embodiments, the values for the expression levels of H2AX in biological samples from both the test subject and the plurality of control subjects may be transformed. For example, the expression levels may be transformed by taking the logarithm of the value. Moreover, the expression levels may be normalized by, for example, dividing by the median expression level among all of the samples.

In certain embodiments, the expression level of microvesicle-associated H2AX in the biological sample from the test subject is increased relative to the expression level of the one or more microvesicle-associated H2AX in biological samples from a plurality of control subjects. In other embodiments, the expression level of microvesicle-associated H2AX in the biological sample from the test subject is decreased relative to the expression level of microvesicle-associated H2AX in biological samples from a plurality of control subjects.

Practicing the Methods

The steps of the method may be practiced by either one or more than one entity. An entity may be, for example, a person, a group of people, an institution, or a business.

One Entity

According to certain aspects, the steps required to practice the method are practiced by one entity. In certain embodiments, a single entity may detect the expression levels of microvesicle-associated H2AX in a biological sample from the test subject and then monitor the cancer treatment or determine the efficacy of cancer treatment. This entity may be, for example, a doctor or a clinician. This entity may also be an institution, such as a hospital or a doctor's office, where all steps of the methods are performed by employees of the institution.

In other embodiments, a single entity may detect the expression levels of microvesicle-associated H2AX in a biological sample from the test subject and communicate the expression levels to a different entity that then monitors the cancer treatment or determines the efficacy of the cancer treatment. In these embodiments, the single entity performing the steps of detecting and communicating may be, for example, a clinic or a lab technician.

More Than One Entity

According to other aspects, the steps required to practice the method may be performed by more than one entity. One entity may detect the expression levels of microvesicle-associated H2AX in a biological sample from the test subject, whereas a different entity may monitor the cancer treatment or determine the efficacy of the cancer treatment. For example, a lab technician at a clinic may detect the expression levels of H2AX in a biological sample from the test subject, and a doctor at a hospital may determine the efficacy of the cancer treatment.

Communication Between Entities

Communication between entities in practicing methods may occur by any means used in the art. Typically, information communicated between entities will be in the form of a report. In certain embodiments, a first entity may obtain expression levels of microvesicle-associated H2AX in a biological sample from the test subject from a second entity that detects the expression levels of microvesicle-associated H2AX in a biological sample from the test subject. The first entity may obtain the expression levels from the second entity directly or indirectly. For example, the first entity may obtain a paper or electronic report of the expression levels directly from the second or different entity. In another example, the first entity may obtain an electronic report of the expression levels on a network to which the second entity has uploaded the report. In yet another example, the first entity may obtain the expression levels from a third entity that has prepared a report from the detections by the second entity.

In other embodiments, a first entity may detect the expression levels of microvesicle-associated H2AX in a biological sample from the test subject and communicate the expression levels to a second or different entity that then monitors the cancer treatment or determines the efficacy of the cancer treatment. The first entity may communicate the expression levels to the second entity directly or indirectly. For example, the first entity may prepare a report with the expression levels and give the report to the second entity manually or electronically. In another example, the first entity may upload the expression levels to a network from which the second entity can obtain the levels. In yet another example, the first entity may communicate the expression levels to a third entity that prepares a report for use by the second entity.

Clinical Trials

Methods described herein may be useful for clinical trials involving cancer. Typically, for their use in clinical trials, the steps required to achieve the objects of the invention will be practiced by more than one entity. For example, multiple entities in different locations, such as clinics in different cities, may detect the expression levels of the one or more microvesicle-associated proteins in a biological sample from the test subject and communicate the expression levels to a different entity, such as a group of doctors directing the clinical trial, who then determine the efficacy of the cancer treatment. In certain embodiments, the multiple entities may use a third entity that prepares and communicates reports of the expression levels to the different entity that determines the efficacy of the cancer treatment. Clinical trials involving the described methods may be useful for evaluating effectiveness of new drugs and treatments for cancer or for evaluating the effects of various clinical parameters on cancer and its progression.

Reagents and Kits

Also provided are reagents and kits thereof for practicing one or more of the above-described methods. The subject reagents and kits thereof may vary greatly. Reagents of interest include reagents specifically designed for use in detection of the above-described expression levels of microvesicle-associated H2AX.

One type of such reagent is an array or kit of antibodies that bind to a biomarker cluster of interest. A variety of different array formats are known in the art, with a wide variety of different probe structures, substrate compositions, and attachment technologies. Representative array or kit compositions of interest include or consist of reagents for quantitation of at least 1 microvesicle-associated protein, such as H2AX.

The kits may further include a software package for statistical analysis of one or more phenotypes, and may include a reference database for calculating the probability of classification. The kit may include reagents employed in the various methods, such as devices for withdrawing and handling blood samples, second stage antibodies, ELISA reagents, tubes, spin columns, and the like.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer-readable medium, e.g., diskette, CD, etc., on which the information has been recorded. Yet another means that may be present is a website address which may be used via the internet to access the information at a removed site. Any convenient means may be present in the kits.

EXAMPLES

The following examples are offered for illustrative purposes and to aid one of skill in better understanding the various embodiments of the disclosure. The following examples are not intended to limit the scope of the present disclosure in any way.

Example 1—Unphosphorylated H2AX and γH2AX as Markers of Genotoxic Stress

The following example demonstrates that microvesicle-derived unphosphorylated H2AX and microvesicle-derived γH2AX are markers of genotoxic stress in a cell. Treatment of U87 brain cancer cells with the DNA alkylating agent temozolomide (TMZ) induced increased abundance of H2AX and γH2AX proteins in microvesicles derived from the U87 cells.

Materials and Methods

Overview of Microvesicles Harvested from Tumor Cell Lines-Experimental Outline

U87 MG (ATCC® HTB14™) cell cultures represent glioblastoma multiforme (GBM). An Integra CELLine Bioreactors (Hudson, N.H.) was seeded from T-75 cultures of U87 into the 15 ml lower chamber, separated by a 10 kDa MWCO filter from a 500 ml upper reservoir chamber. After growth was established in the lower chamber containing exosome free fetal bovine serum (Exo-FBS Systems Biosciences, Mountain View Calif.), supernatant samples were recovered on a weekly basis. Upper chambers of the bioreactors were replenished with normal fetal serum-containing medium. The cultures used were between 4 and 5 months old and were monitored for continued robust health.

On day 1 of the study, the Integra bioreactor was provided with normal Eagles minimal essential medium (EMEM) supplemented with exosome-free fetal bovine serum FBS. Additionally fresh media was added to the upper chamber. Supernatant samples were taken at 2, 4, 6, and 24 hours after addition of fresh medium, mixed with protease inhibitor and Venceremin peptide reagent (New England Peptide, Gardner, Mass.) for incubation at 4° C.

Culture supernatants were collected at 24 hours. Fresh medium was added to both the lower and upper chamber adjusted to 100 µm TMZ was added (day 2) and supernatant samples taken as indicated above. The process was repeated at 48 hours with the exception that fresh media had been adjusted to 300 µm TMZ (day 3). The final collection of lower chamber supernatant occurred at 72 h.

Microvesicles in the conditioned media were recovered from culture supernatants using one of the Venceremin peptides (New England Peptide, Gardner Mass.). Venceremins were originally identified as ligands with strong avidity for heat shock proteins, particularly HSP90 and of variable affinity to isoforms of HSP70, HSP60 and other chaperone proteins. Microvesicles from pathologically affected cells, particularly cancer, display HSPs on the external surface. To recover microvesicles, the Venceremin peptide Vn96reverse, referred to as Heladonin (Hdn: H2N-LKLFEGLTLAGWSFRSLSLGRGKGQSP-OH) (SEQ ID NO: 1), was used. The Integra bioreactor lower chamber supernatant samples (2 mls) were mixed with 10 µl of protease inhibitor and 50 µg of Hdn peptide stock solution. Microvesicles were prepared from Bioreactor supernatant samples taken at 2, 4, 6 and 24 hours after addition of fresh medium and placed at 4° C.

All samples were incubated for at least 18 h. The samples were processed by centrifugation (4500 g) washing in 1 ml of PBS and repeat centrifugation. The presence of U87 microvesicles in material pelleted from the lower chamber of the cell cultures was determined by Western blotting.

Cell Culture Media

Exosome-free fetal bovine serum (FBS) supplement was purchased from Exo-FBS Systems Biosciences, Mountain View Calif. Eagles minimal essential medium (EMEM) supplied by ATCC Cat #30-2003. Complete 10% fetal bovine serum 90% EMEM was placed in the upper reservoir chamber of the CELLine Bioreactor. Prior to introduction of U87 cells into the bioreactor, the bioreactor was provided with Eagle's minimum essential medium+100 U/ml penicillin+100 µg/ml streptomycin (EMEM)+10% exosome-free fetal bovine serum FBS. After U87 cell introduction into the bioreactor, the bioreactor was cultured at 37° C. in a 5% carbon dioxide atmosphere. Upper chamber contains EMEM supplemented regular fetal bovine serum. A control bioreactor containing 15 mls of EMEM+Exo-free Medium placed at 37° C. was used. 2 mls were taken from the controls each day and replaced with fresh medium.

Temozolomide (TMZ) Preparation

The MW of TMZ is 194.151 g/mol. 100 mg TMZ was dissolved in 5 ml of DMSO (20 mg/ml TMZ), which is equivalent to 20 µg/µl TMZ (257 mM). The stock solution of TMZ was used to provide TMZ at designated concentrations in the culture media of the bioreactor.

Day 1 Protocol—Introduction of Fresh Serum-EMEM to Bioreactor Culture (No TMZ)

The culture received fresh SBI Exosome-free serum supplemented media in lower chamber and regular FBS-supplemented media in the upper chamber and placed in a 37° C. incubator. At 2, 4 and 6 h the bioreactor was retrieved from the incubator and rocked gently for 1 min. 2 mls of media were removed from the lower cell chamber and transferred to 2.0 ml HANDEE microcentrifuge tube (PIERCE Rockland Ill.) containing 5 ul of protease inhibitor (Cocktail III, EMD Merck Millipore). 2 mls of fresh media was added to upper chamber to compensate for removal. The retrieved volumes of supernatant (SN) were centrifuged at 17000 g for 5 m at 4° C. to pellet microparticulates and cell debris. 1.8 ml supernatant was transferred to a new tube taking care to avoid any pelleted material. The SN was mixed with 10 µl of Hdn peptide stock solution and incubated at 4° C. overnight for microvesicle recovery. The cell and microparticle pellet (17000 g) was stored at −80° C.

Day 2 Protocol-Recovery of Microvesicle Population and Introduction of New Media Containing 100 µM TMZ After 24 h the bioreactor flask was retrieved from incubators and rocked gently for 5 m. All of the culture medium was retrieved from the lower cell chamber and immediately replaced with fresh EMEM with Exo-FBS containing 100 µM TMZ stock solution. 100 µM TMZ was also added to the upper chamber.

For the 24 hour microvesicle sample, 2 ml samples of SN were transferred to HANDEE tubes containing 50 of protease inhibitor as for the 2, 4 and 6 h samples and placed at 4° C. All remaining culture SN was frozen at −80° C. The cell free solutions serving as negative controls were also processed in an identical manner.

Day 3 Protocol—Recovery of Microvesicle Population and Introduction of New Media Containing 300 µM TMZ Replacement of media and processing of samples for the collection of microvesicles was conducted in the same manner as day 2 with the exception that serum-supplemented EMEM was adjusted to 300 µM TMZ in both upper and lower chambers of the CELLine Bioreactor.

Day 4 Protocol—Final Collection of Culture Supernatant

Replacement of media and processing of samples for the collection of microvesicles was conducted in the same manner as day 2 with the exception that no further addition of TMZ was given to the cultures and the collection of lower chamber supernatant was considered the end of the experiment. The accumulated microvesicle samples were stored at 4° C. for a minimum of 18 h for processing together on day 5 in preparation for gel electrophoresis.

Preparation of Microvesicles

All SN samples stored at 4° C. with Hdn peptide and protease inhibitor were centrifuged at 4500 g for 5 m at 4° C. The SNs were utilized to isolate the microvesicle pellets. Protein pellets were resuspended in 1 ml of PBS by vortexing and returned to the microcentrifuge for 5 m at 4500 g at 4° C. Protein pellets were prepared for electrophoresis by resuspension in a variant of Laemmli SDS buffer as previously described (Wubbolts et al., 2003). The premixed 4×XT loading buffer (Bio-Rad) was adjusted to 4M urea, 25 mM TCEP (reducing agent; PIERCE) and 5 µl/ml of protease inhibitor (Cocktail III EMD Milipore). The electrophoresis sample/loading buffer was referred to as "USB" for urea sample buffer. Samples were incubated at 95° C. in a dry-heating block for 5 minutes, vortexed vigorously and given a 30 s spin in a microcentrifuge to bring down droplets and condensation.

Electrophoresis and Blotting Conditions

Frozen samples in SDS/Urea electrophoresis buffer were incubated at 95° C. for 30 seconds, vortexed and microfuged briefly. 250 volumes were applied to 10% XT Bis-Tris Criterion precast midi gels in XT-MES running buffer (all products Bio-Rad Hercules Calif.). Gels were run in Criterion modules (Bio-Rad) for approximately 55 minutes at 150 V. After electrophoresis was complete, the gels were rinsed in Towbin transfer buffer and layered onto supported nitrocellulose, blotting pads and paper (BioRad), all assembled into a blotting cartridge for insertion in the Criterion blotting module. The blotting module contained pre-chilled Towbin transfer buffer and an ice pack. Blotting was considered complete by running at 90V for 30 m. The blot was rinsed in distilled deionised water and processed with the Pierce reversible protein stain kit. The images were captured using a Bio-Rad Chemi-Doc using white light mode and allowed to dry.

Antibody Reactivity and Image Generation

The blots were destained to clear background by rehydration in ddH2O and use of destaining reagent (PIERCE). The blots were blocked for 30 minutes in 5% low-fat skim milk powder dissolved in phosphate buffered saline adjusted to 0.075% Tween 20 (TPBS).

The blots were cut longitudinally at the 37 kDa marker (i.e. perpendicular to the direction of electrophoresis) to allow for the same samples to be probed for low molecular weight (bottom) and high molecular weight proteins (top). In this instance the target was gamma γH2AX (~17 kDa Anti-phospho-Histone H2A.X_Ser139: Millipore MABE205). After reactivity to these antibodies had been recorded, the same blots were incubated with a secondary sequence of H2AX (i.e. unphosphorylated H2AX anti-Histone H2A.X: Millipore 07-627).

Primary antibody was mixed with 3% milk dissolved in TPBS at a 1:2000 dilution and the blot incubated for 60 minutes, washed 4 times with an equal volume of TPBS, incubated by a 1:2000 dilution of horse-radish peroxidase (HRP) secondary antibody, washed 4 times for 10 minutes with TPBS. All incubations rocking and washes were conducted automatically with a Freedom Rocker device (Next Advance, Averil Park N.Y.). The antibody-probed and TPBS washed blot halves were covered with 1 ml of Super Signal West Dura HRP substrate (PIERCE), covered with cling film and imaged using the Chemi-Doc at exposures between 2 s and 60 s depending on the signal intensity.

Growth Conditions for U87 Cultures Used in Subcellular Protein Analysis

U87 cell cultures were grown as a monolayer in T-75 flasks (Corning, 75 cm², ultra low attachment surface). Flask 1 was designated as a control flask, while Flasks 2 and 3 were treated with 50 µM and 100 µM TMZ, respectively. U87s were grown in Eagle's Minimum Essential Medium, fetal bovine serum to a final concentration of 10%. Cells were grown to 80% prior to dosage with TMZ.

Subcellular Fractionation and Compartment Isolation

Control and TMZ-treated U87 cells were processed into subcellular fractions using the sub-cellular proteome extraction kit (S-PEK, EMD Milipore) according to manufacturer instructions using differential detergent extraction with four extraction buffers to isolate proteins enriched in various cellular compartments. Various buffers were used in the extraction process to enrich for proteins in specified compartments as follows: from the cytoplasmic compartment in Extraction buffer 1 (EB1); enriched in membrane-associated proteins, Extraction buffer 2 (EB2); enriched in nucleus-associated proteins, Extraction buffer 3 (EB3) or enriched in cytoskeletal proteins, Extraction buffer 4 (EB4). All blots on cellular compartment-extracted proteins were conducted as described for microvesicle-isolated proteins.

Results

H2AX and γH2AX are Markers of Genotoxic Stress

Figure 2:
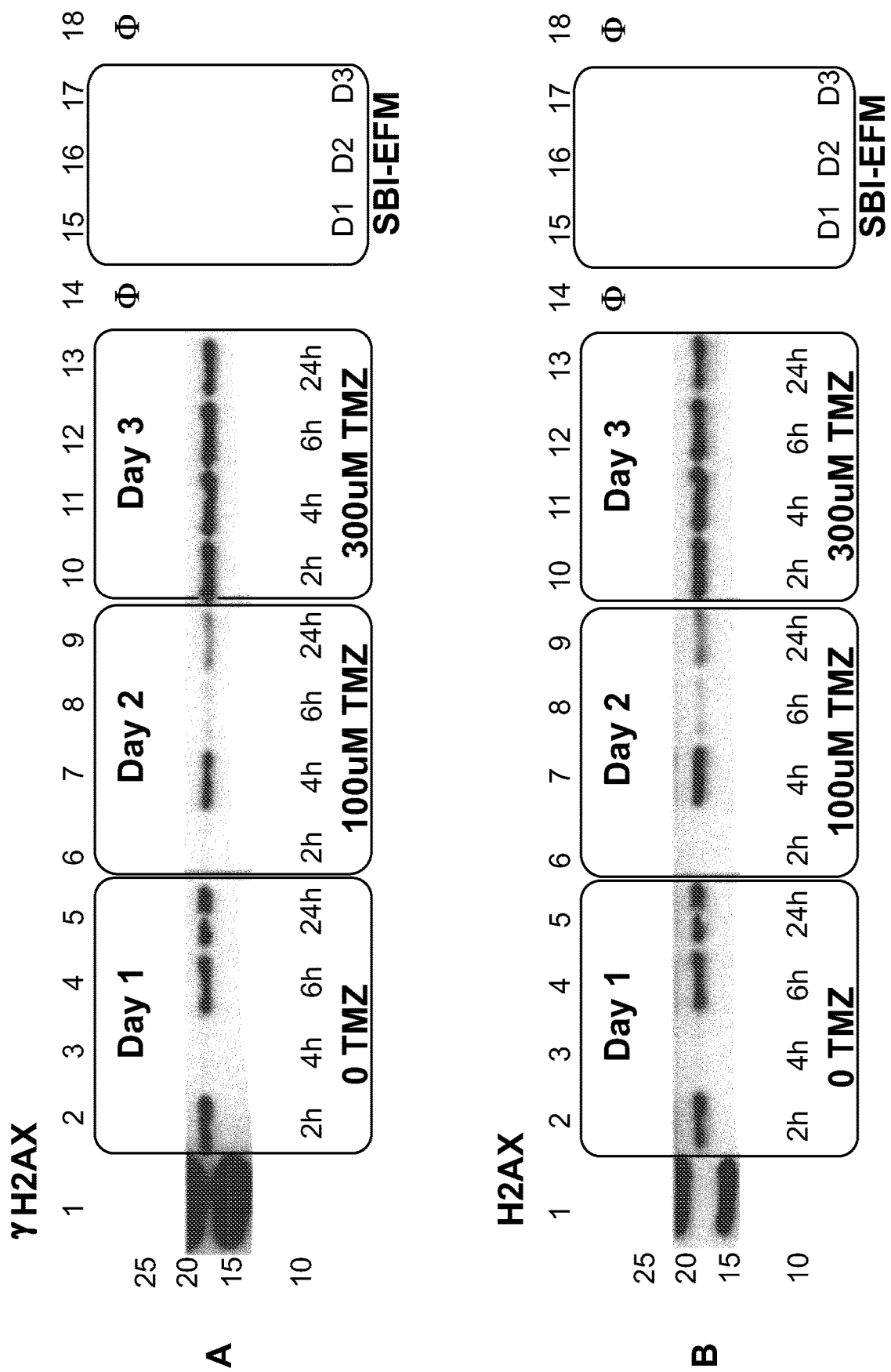
FIG. 2A illustrates a Western blot analysis of γH2AX protein present in the various microvesicle samples.
FIG. 2B illustrates a Western blot analysis of H2AX protein present in the various microvesicle samples.

Table 2 illustrates the microvesicle samples analyzed in the blot analyses and the corresponding lanes for the respective samples, the results of which are depicted in FIG. 1 and FIG. 2A, 2B.

TABLE 2

Identification of Microvesicle Samples in the Specified Blot Lanes

| Lane # | U87 Media and MCVS Harvested from Exosome Free Culture Media |
|---|---|
| 1 | 5X dilution of MW standard |
| 2 | Controls + (SBI) 2 hours |
| 3 | Controls + (SBI) 4 hours |
| 4 | Controls + (SBI) 6 hours |
| 5 | Controls + (SBI) 24 hours |
| 6 | (SBI + 100 μm TMZ) 2 hours |
| 7 | (SBI + 100 μm TMZ) 4 hours |
| 8 | (SBI + 100 μm TMZ) 6 hours |
| 9 | (SBI + 100 μm TMZ) 24 hours |
| 10 | (SBI + 300 μm TMZ) 2 hours |
| 11 | (SBI + 300 μm TMZ) 4 hours |
| 12 | (SBI + 300 μm TMZ) 6 hours |
| 13 | (SBI + 300 μm TMZ) 24 hours |
| 14 | Blank |
| 15 | Control SBI Media 0 |
| 16 | Control SBI Media 1 |
| 17 | Control SBI Media 2 |
| 18 | Blank |

All samples appeared closely matched in overall intensity of total protein profile, with subtle variation in protein intensity at higher (e.g. ~250 kDa) and lower (10-25 kDa) molecular weight (FIG. 1, lanes 2-13). Protein was also recovered from the exosome-free serum product in the absence of cell material (FIG. 1, lanes 15-17; SBI-EFM).

For γH2AX (FIG. 2A), a band migrating between the 15 and 20 kDa marker was clearly observed at 2, 6 and 24 h after medium replacement, with only a thin band seen at 4 h (FIG. 2A, lanes 2,4, 5 and 3). However, γH2AX was uniformly intense in 2, 4, 6 and 24 h microvesicles on day 3 following addition of 300 uM temozolomide (TMZ) to the culture media. This study therefore presents the first recorded observation of γH2AX, a nuclear biomarker reflecting alkylation of DNA, captured in shed microvesicle material. Without wishing to be bound by theory, it is believed that the identification of γH2AX on the first day, in the absence of the DNA damaging agent (TMZ), supports the observation that the U87 phenotype is associated with genomic instability due to the observed release of γH2AX in microvesicles. After 3 days of exposure to TMZ, γH2AX became consistent in intensity and was more abundant following addition of TMZ to the culture media. This latter observation indicates that prolonged exposure to TMZ increases the probability that γH2AX will be incorporated into microvesicles. γH2AX in microvesicles may thus be used as an indicator of phenotypic genomic instability and increased DNA damage due to drug or radiation exposure.

For H2AX (FIG. 2B), the antibody to unphosphorylated H2AX was used secondarily to the same blot probed for γH2AX. It was observed that the protein expression of H2AX, even in the presence of TMZ, was similar to that observed for γH2AX. H2AX in microvesicles may thus be used as an indicator of phenotypic genomic instability and increased DNA damage due to drug or radiation exposure.

H2AX and γH2AX are Nuclear Proteins

Figure 3:
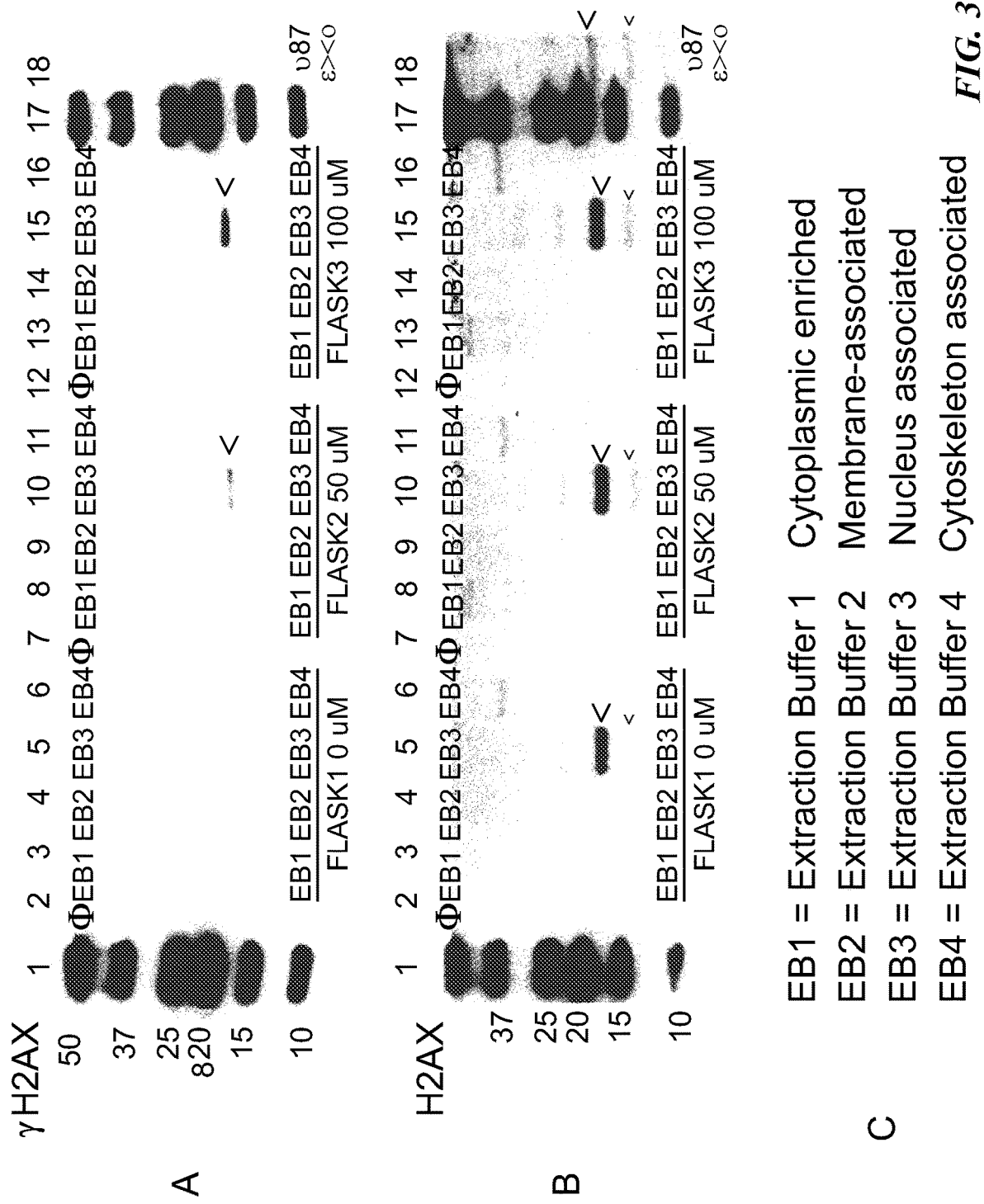
FIG. 3A illustrates a Western blot analysis of γH2AX protein present in various subcellular compartment samples from cells of the U87 tumor colony.
FIG. 3B illustrates a Western blot analysis of H2AX protein present in various subcellular compartment samples.
FIG. 3C illustrates a legend of the subcellular compartments analyzed in the blot and their respective labels.

Table 3 illustrates the subcellular compartment samples analyzed in the blot analyses and the corresponding lanes for the respective samples, the results of which are depicted in FIG. 3.

TABLE 3

Identification of Subcellular Compartment Samples in the Specified Blot Lanes

| Lane # | T-75 Monolayer Flasks |
|---|---|
| 1 | 5X dilution of MW standard |
| 2 | Blank |
| 3 | 0 μM TMZ, EB1 |
| 4 | 0 μM TMZ, EB2 |
| 5 | 0 μM TMZ, EB3 |
| 6 | 0 μM TMZ, EB4 |
| 7 | Blank |
| 8 | 50 μM TMZ, EB1 |
| 9 | 50 μM TMZ, EB2 |
| 10 | 50 μM TMZ, EB3 |
| 11 | 50 μM TMZ, EB4 |
| 12 | Blank |
| 13 | 100 μM TMZ, EB1 |
| 14 | 100 μM TMZ, EB2 |
| 15 | 100 μM TMZ, EB3 |
| 16 | 100 μM TMZ, EB4 |
| 17 | 5X dilution of MW standard |
| 18 | U87 control |

As can be seen in FIG. 3A, γH2AX protein could only be detected in nuclear fractions of U87 protein extracts from whole cells, as represented by the single detected band marked with an arrow. γH2AX protein also began to accumulate only in the nucleus following application of TMZ to the cell culture. Similarly, and as can be seen in FIG. 3B, H2AX protein could only be detected in nuclear fractions of U87 protein extracts from whole cells (large arrow). A smaller protein was also detected in nuclear extracts (small arrow) with an H2AX antibody, possibly representing a degradation product or fragment of H2AX.

In summary, both γH2AX and H2AX proteins could only be detected in nuclear fractions of U87 cells, as these proteins were absent from protein extracts enriched for cytoplasmic, membrane-associated, and cytoskeletal proteins. These data confirm that both γH2AX and H2AX are nuclear-localized proteins and confirm that the source of the exosomal signal for γH2AX appears not to be derived from cytoplasmic or membrane bound protein.

Example 2—Unphosphorylated H2AX and γH2AX as Tumor Markers

The following example demonstrates that microvesicle-derived unphosphorylated H2AX and microvesicle-derived γH2AX, which are both histone proteins, are relevant tumor markers. These protein markers were found to be associated with microvesicles shed from various tumor or tumor-like cell lines, including a cervical cancer model cell line (HELA), a glioma model cell line (U87), and a model highly proliferative renal cell line (HEK293T).

Materials and Methods

Overview of Microvesicles Harvested from Tumor Cell Lines-Experimental Outline

HELA (ATCC® ccl-2™), U87 (ATCC® HTB14™), and HEK293T (ATCC® CRL-1573™) cell cultures were grown in Integra CELLine Bioreactors (Hudson, N.H.) after seeding from T-75 cultures into the 15 ml lower chamber, separated by a 10 kDa MWCO filter from a 500 ml upper reservoir chamber. After growth was established in the lower chamber containing exosome free fetal bovine serum (Exo-FBS Systems Biosciences, Mountain View Calif.), supernatant samples were recovered on a weekly basis. Upper chambers of the bioreactors were replenished with normal fetal serum-containing medium. The cultures used were between 4 and 5 months old and were monitored for continued robust health.

Microvesicles in the conditioned media were recovered from culture supernatants using Venceremin peptides (Vn96, New England Peptide, Gardner Mass.) in conjunction with a variety of wash buffers for the disaggregation of microvesicles prior to use of Vn96. Microvesicles from these cells were harvested in the conditioned media from the Integra bioreactor lower chamber and supernatant samples (2 mils) were mixed with 10 µl of protease inhibitor and 50 µg of Vn96 peptide stock solution, Microvesicles were prepared from Bioreactor supernatant samples taken at 2, 4, 6 and 24 hours after addition of fresh medium and placed at 4° C.

Cell Culture Medium

Exosome-free fetal bovine serum (FBS) supplement was purchased from Exo-FBS Systems Biosciences, Mountain View Calif. Eagles minimal essential medium (EMEM) supplied by ATCC Cat #30-2003. Complete 10% fetal bovine serum 90% EMEM was placed in the upper reservoir chamber of the CELLine Bioreactor. Prior to introduction of cells into the bioreactor, the bioreactor was provided with Eagle's minimum essential medium+100 U/ml penicillin+ 100 µg/ml streptomycin (EMEM)+10% exosome-free fetal bovine serum FBS. After cells were introduced into the bioreactor, the bioreactor was cultured at 37° C. in a 5% carbon dioxide atmosphere. Upper chamber contains EMEM supplemented regular fetal bovine serum.

Preparation of Microvesicles

Figure 4:
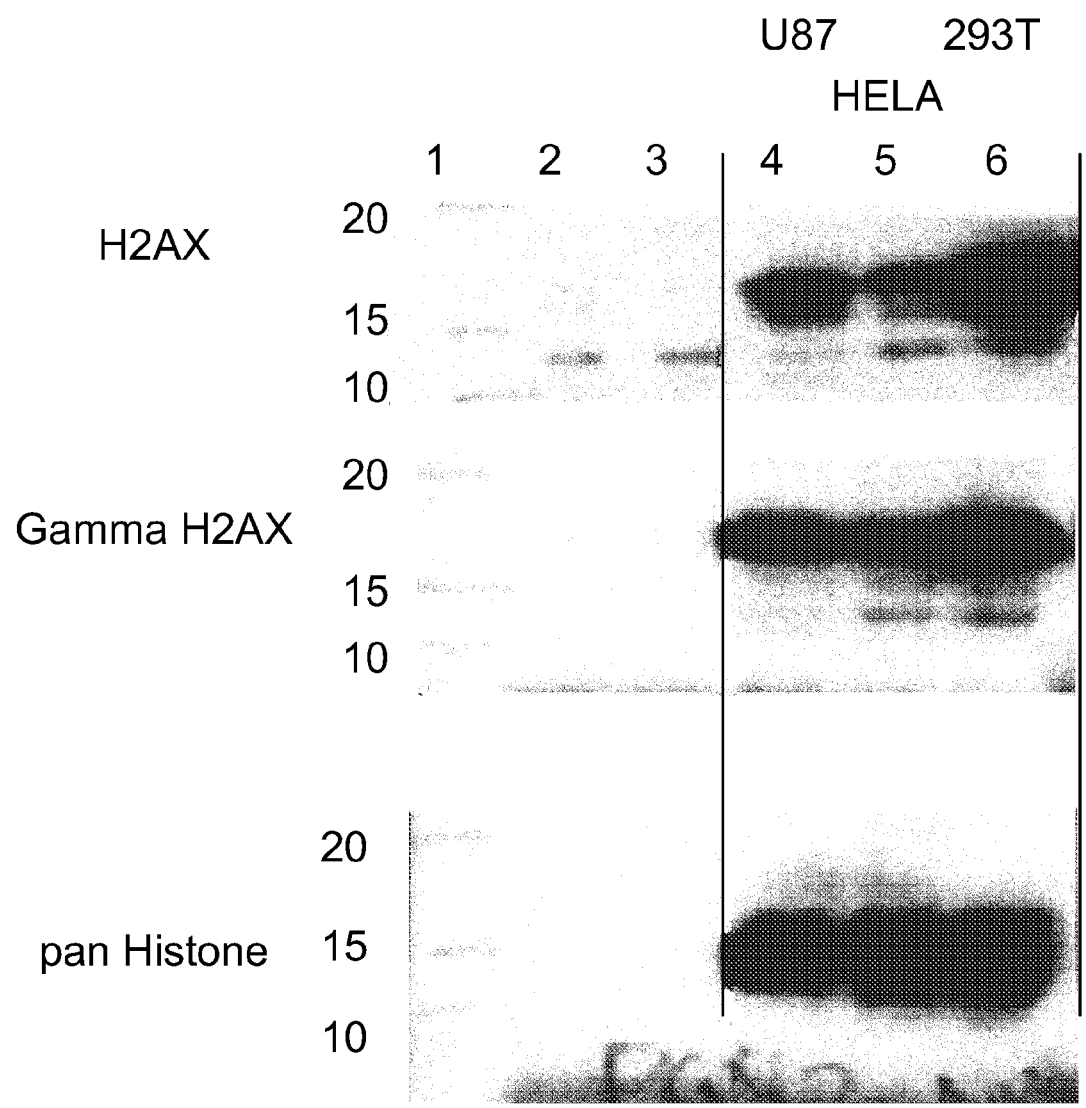
FIG. 4 illustrates a Western blot analysis of H2AX, γH2AX, and pan-Histone proteins present in microvesicle preparations from U87, Hela, and HEK293T cells under various conditions.

Raw Stock Solutions containing U87, HELA, or HEK293T (293T) bioreactor culture medium were concentrated by VivaSpin 1 million Dalton molecular weight cut off (MWCO) spin filters and resuspended in 50 mM amino acid solution (Stock B) or 5% detergent (Stock D). These solutions were prepared for electrophoresis directly by adding 50 µl of 3× urea SDS sample buffer (USB) to 100 µl of the stock solutions. After heating at 95° C., 15 µl were loaded. Samples of Stock 13 and Stock D can be seen in lanes 2 and 3 of each blot (FIG. 4).

Peptide recovered microvesicles using Vn96 (microvesicle samples) were prepared by incubating 1.8 ml volumes of CELLiNE Integra bioreactor culture media from U87, HELA, or 293T cells with 50 µg of peptide overnight at 4° C. After incubation of the mixtures were centrifuged at 4500 g washed by resuspending in 500 µl of Stock B and re-pelleted by centrifugation. The supernatant was removed and the pellet resuspended in 200 µl of 1× urea SDS sample buffer (USB). 15 µl were loaded to the gel. U87, HELA and 293T microvesicle samples are shown in lanes 4-6 of FIG. 4. Other samples in FIG. 4 were collected by PD-10 size exclusion chromatography (SEC) using 2% agarose beads and selected buffers.

1 ml sample volumes and 1 ml eluate fractions were collected by gel filtration procedure PD-10 SEC as discussed herein to form the contents of peak 1 (fractions 2, 3, 4, and 5). For the analysis, fractions 2 and 3 were reduced to minimal volume in a VivaSpin 2 ml 1 million Dalton molecular weight cut off (MWCO) spin filter; fractions 4 and 5 were added on top of the retentate of 2 and 3 and again centrifuged to minimum volume. Samples consisting of fractions 2, 3, 4, and 5, otherwise known as peak 1, were pooled and resuspended in 1 ml of water. The remaining 500 µl was centrifuged to minimum volume and resuspended in 150 µl of 1× urea SDS sample buffer (USB). 150 were loaded to the gel. The concentrated pooled peak 1 fractions were prepared from U87 bioreactor culture medium that had been concentrated by VivaSpin 1 million Dalton molecular weight cut off (MWCO) spin filters and resuspended in AB Serum (Stock A) as indicated above following the PD-10 fractionation into 1 ml volumes fractions 2, 3, and 4.

Mass Spectrometry Protein Analysis

U87 preparations were resuspended into Serum A/B and microvesicles isolated using gel filtration. Microvesicle particles were isolated and subjected to protein isolation and tryptic digest. Microvesicle fractions were run on an on 8%, 10%, and 12% T columns using the GELFrEE system (Protein Discovery), collecting 12 fractions per column. GELFrEE fractions were processed by acetone precipitation for SDS removal according to the method described in Botelho et al. (2010). Fractions were analyzed via bottom-up LC-MS/MS on a Thermo LTQ mass spectrometer and identified using Scaffold (Proteome Software) and Bioworks, and quantified via spectral counting according to Yates et al. (2004).

Electrophoresis and Blotting Conditions

Frozen samples in SDS/Urea electrophoresis buffer were incubated at 95° C. for 30 seconds, vortexed and microfuged briefly. 250 volumes were applied to 10% XT Bis-Tris Criterion precast midi gels in XT-MES running buffer (all products Bio-Rad Hercules Calif.). Gels were run in Criterion modules (Bio-Rad) for approximately 55 minutes at 150 V. After electrophoresis was complete, the gels were rinsed in Towbin transfer buffer and layered onto supported nitrocellulose, blotting pads and paper (BioRad), all assembled into a blotting cartridge for insertion in the Criterion blotting module. The blotting module contained pre-chilled Towbin transfer buffer and an ice pack. Blotting was considered complete by running at 90V for 30 m. The blot was rinsed in distilled deionised water and processed with the Pierce reversible protein stain kit. The images were captured using a Bio-Rad Chemi-Doc using white light mode and allowed to dry.

Antibody Reactivity and Image Generation

The blots were destained to clear background by rehydration in ddH2O and use of destaining reagent (PIERCE). The blots were blocked for 30 minutes in 5% low-fat skim milk powder dissolved in phosphate buffered saline adjusted to 0.075% Tween 20 (TPBS).

The blots were cut longitudinally at the 37 kDa marker (i.e. perpendicular to the direction of electrophoresis) to allow for the same samples to be probed for low molecular weight (bottom) and high molecular weight proteins (top). In this instance the target was gamma γH2AX (~17 kDa Anti-phospho-Histone H2A.X_Ser139: Millipore MABE205). After reactivity to these antibodies had been recorded, the same blots were incubated with a secondary sequence of H2AX (i.e. unphosphorylated H2AX anti-Histone H2A.X: Millipore 07-627). In a separate series of gels, the blots were probed for the presence of pan Histones using the Anti-Histone H4 Antibody: Millipore 04-858.

Primary antibody was mixed with 3% milk dissolved in TPBS at a 1:2000 dilution and the blot incubated for 60 minutes, washed 4 times with an equal volume of TPBS, incubated by a 1:2000 dilution of horse-radish peroxidase (HRP) secondary antibody, washed 4 times for 10 minutes with TPBS. All incubations rocking and washes were conducted automatically with a Freedom Rocker device (Next Advance, Averil Park N.Y.). The antibody-probed and TPBS washed blot halves were covered with 1 ml of Super Signal West Dura HRP substrate (PIERCE), covered with cling film and imaged using the Chemi-Doc at exposures between 2 s and 60 s depending on the signal intensity.

Results

Table 4 illustrates the microvesicle samples analyzed in the blot analyses and the corresponding lanes for the respective samples, the results of which are depicted in FIG. 4.

TABLE 4

Microvesicle Samples in the Specified Blot Lanes

| Lane # | Condition/Source of Protein |
|---|---|
| 1 | Molecular weight markers |
| 2 | U87 in 50 mM amino acid solution (Stock B) |
| 3 | U87 in 5% detergent (Stock D) |
| 4 | U87 microvesicle sample |
| 5 | HELA microvesicle sample |
| 6 | HEK293T microvesicle sample |

The blots described above were probed to detect specific proteins in the various samples (See Table 4 and FIG. 4). In all instances with the exception of CD63, the detection of all proteins was strongest in the peptide recovered microvesicle fractions (microvesicle samples). Antibodies to all histones (pan-histone), H2AX, and γH2AX were strongly represented in the microvesicle samples (lanes 4, 5, and 6), but could not be detected in the stock solution lanes (lanes 2 and 3), which were obtained from cell culture samples and not enriched for microvesicles. Histones are a surface feature of rapidly dividing cells, such as cancers. The data presented in FIG. 4 suggests that histones are incorporated into shed microvesicles from tumor cells. Without wishing to be bound by theory, it is also thought that, as histones may be part of nucleosomes, they may be shed from the cells in membranous form. The rich presence of histones in the tumor cell-derived microvesicle samples could also be detected by analysis with mass spectrometry, as shown in Table 5 below.

TABLE 5

Identification of Histones in Microvesicle Samples by OMS

| Gene | Description | Peps | kDa |
|---|---|---|---|
| HIST1H2BK | Histone H2B type 1-K | 4 | 14 |
| HIST2H2AC | Histone H2A type 2-C | 4 | 14 |

Although the total protein load indicates that proteins from the microvesicle samples are loaded in equal amounts, U87 is identified as being the strongest in association with the well-known canonical marker CD63. However although widely regarded as an archetypic marker, CD63 is not strongly expressed on HELA or 293T.

In summary, the data reveals that histone proteins, such as H2AX and γH2AX, are enriched in tumor-derived microvesicles. This suggests that histone proteins may be useful as tumor markers.

REFERENCES

Wubbolts R, Leckie R S, Veenhuizen P T, Schwarzmann G, Möbius W, Hoernschemeyer J, Slot J W, Geuze H J, Stoorvogel W. *J Biol Chem.* 2003 Mar. 28; 278(13): 10963-72.
Taylor, C. G., Atay, S., Tullis, R. H., Kesimer, M and Taylor, D. D. *Anal. Biochem.* 2012, 28(1): 44-53.
Botelho et al. J. Proteome Res. 2010, 9, 2863-2870.
Yates et al. Anal. Chem. 2004, 76, 4193-4201.

The invention claimed is:

1. A method of monitoring and continuing cancer treatment in an individual determined to exhibit inhibition of DNA replication in cancer cells induced by previous cancer treatment, the method comprising:
   a) providing cancer treatment to a test subject, wherein the cancer treatment comprises exposure to radiation and/or administration of an anti-cancer agent, wherein the anti-cancer agent is selected from the group consisting of a platinum analogue, a tetrazine, an anti-metabolite, a plant alkaloid or terpenoid, cytotoxic antibiotic, and a DNA alkylating agent;
   b) isolating cancer-derived microvesicles from a biological sample from the test subject;

c) detecting the expression level of variant of histone protein H2A (H2AX) in the cancer-derived microvesicles;

d) determining whether there is a higher level of expression of H2AX in cancer-derived microvesicles from the test subject as compared to the level of H2AX in cancer-derived microvesicles isolated from a control subject that is not given the cancer treatment;

e) selecting the test subject having, as determined by step (d), a higher level of expression of H2AX in the cancer-derived microvesicles as compared to a control subject that is not given the cancer treatment; and f) monitoring the treatment comprising continuing the cancer treatment in the test subject selected in (e).

2. The method of claim 1, wherein the DNA alkylating agent is temozolomide.

3. The method of claim 1, wherein the anti-cancer agent is a type I topoisomerase inhibitor.

4. The method of claim 3, wherein the type I topoisomerase inhibitor is an indenoisoquinoline.

5. The method of claim 1, further comprising repeating the isolating, detecting, determining, and continuing steps at a plurality of time points following administration of the cancer treatment to the test subject.

6. The method of claim 1, wherein the cancer comprises a solid tumor.

7. The method of claim 1, wherein the cancer is selected from the group consisting of pancreatic, ovarian, adenocarcinoma, prostate, breast, brain, head, neck, renal, lung, central nervous system and lymphoma cancers.

8. The method of claim 1, wherein the cancer is brain cancer.

9. The method of claim 8, wherein the brain cancer is glioblastoma multiforme.

10. The method of claim 1, wherein the biological sample is selected from the group consisting of plasma, serum, cerebrospinal fluid, urine, tears, milk, lymph fluid, synovial fluid, bronchoalveolar lavage, amniotic fluid, saliva, ocular fluid, ascites, and respiratory droplets.

11. The method of claim 1, wherein detecting the expression level of H2AX comprises the use of ELISA, flow cytometry, or liquid chromatography-mass spectrometry.

12. The method of claim 1, wherein detecting the expression level of H2AX comprises detecting binding of H2AX to an H2AX-specific antibody.

13. The method of claim 12, wherein the antibody is covalently bound to a bead.

14. The method of claim 12, wherein detecting binding comprises detecting fluorescence.

15. The method of claim 1, wherein isolating cancer-derived microvesicles is achieved via affinity capture using a venceremin polypeptide, a reagent specific to tenascin-C, a reagent specific to a tetraspanin, a reagent specific to a heat shock protein, or a reagent specific to annexin.

16. The method of claim 1, wherein the H2AX is γH2AX.

* * * * *